(12) United States Patent
Ohmer et al.

(10) Patent No.: US 10,925,766 B2
(45) Date of Patent: Feb. 23, 2021

(54) SAFETY CLOSURE FOR A HOT-WATER BOTTLE

(71) Applicant: WFI WÄRMFLASCHENINNOVATION UG (HAFTUNGSBESCHRÄNKT), Gröbenzell (DE)

(72) Inventors: Benjamin Ohmer, Munich (DE); Volker Junior, Grafelfing (DE); Laura Diez, Kempten (DE); Anja Krautter, Albstadt (DE)

(73) Assignee: WFI WÄRMFLASCHENINNOVATION UG (HAFTUNGSBESCHRÄNKT), Munich (DE)

( * ) Notice: Subject to any disclaimer, the term of this patent is extended or adjusted under 35 U.S.C. 154(b) by 671 days.

(21) Appl. No.: 15/537,923

(22) PCT Filed: Dec. 18, 2015

(86) PCT No.: PCT/EP2015/080681
§ 371 (c)(1),
(2) Date: Nov. 10, 2017

(87) PCT Pub. No.: WO2016/097386
PCT Pub. Date: Jun. 23, 2016

(65) Prior Publication Data
US 2018/0125704 A1  May 10, 2018

(30) Foreign Application Priority Data

Dec. 20, 2014 (DE) .......................... 10 2014 119 307
Feb. 10, 2015 (DE) .......................... 10 2015 101 853
(Continued)

(51) Int. Cl.
*A61F 7/08* (2006.01)
*A61F 7/10* (2006.01)

(52) U.S. Cl.
CPC ........ *A61F 7/086* (2013.01); *A61F 2007/105* (2013.01)

(58) Field of Classification Search
CPC ................................ B65D 39/08; A61F 7/086
(Continued)

(56) References Cited

U.S. PATENT DOCUMENTS 992,928 A * 5/1911 Walcott .......................... 215/356
1,478,918 A * 12/1923 Rupp ..................... B65D 39/08
217/110
(Continued)

FOREIGN PATENT DOCUMENTS

AU 2004200830 3/2004
CA 2372648 A1 8/2003
(Continued)

OTHER PUBLICATIONS

Office Action from the Chinese Patent Office dated Feb. 22, 2019 in related Chinese application No. 201580069848.2, and machine translation thereof.
(Continued)

*Primary Examiner* — Anthony D Stashick
*Assistant Examiner* — Raven Collins
(74) *Attorney, Agent, or Firm* — J-Tek Law PLLC; Jeffrey D. Tekanic; Scott T. Wakeman

(57) ABSTRACT

A multi-part safety closure for a hot-water bottle includes at least one closure part (4) having an external screw thread (12) for screwing into an internal screw thread of a hot-water bottle and having a first force transmission element (6) for transmitting force for screwing and unscrewing the closure part (4) into and out of, respectively, the internal screw
(Continued)

thread of the hot-water bottle (14) to seal the bottle (14) in a water-tight manner; and a manual actuating element (2) having a second force transmission element (8) for transmitting to the closure part (4) the force required to screw and unscrew the closure part (4) into and out of, respectively, the internal screw thread (17). The first force transmission element (6) and the second force transmission element (8) are configured such that the closure part (4) is operably connectable with the manual actuating element (2) in a detachable manner.

6 Claims, 13 Drawing Sheets

(30) Foreign Application Priority Data

| | | | |
|---|---|---|---|
| Aug. 26, 2015 | (DE) | ......................... | 10 2015 114 180 |
| Sep. 2, 2015 | (DE) | ......................... | 10 2015 114 671 |
| Oct. 8, 2015 | (DE) | ......................... | 10 2015 117 217 |

(58) Field of Classification Search
USPC .................................................. 215/356, 302
See application file for complete search history.

(56) References Cited

U.S. PATENT DOCUMENTS

| | | | |
|---|---|---|---|
| 1,737,605 A | 12/1929 | Mauser | |
| 1,810,795 A | 6/1931 | Soderquist | |
| 2,439,907 A | 4/1948 | Poglein | |
| 2,718,250 A * | 9/1955 | Bradford | ................. A61F 7/086 383/80 |
| 3,216,632 A | 11/1965 | Dearing | |
| 4,169,493 A | 10/1979 | Segalowicz | |
| 4,580,547 A | 4/1986 | Kapralis et al. | |
| 5,114,032 A | 5/1992 | Laidlaw | |
| 6,302,902 B1 | 10/2001 | Benja-Athon | |
| 6,692,146 B1 | 2/2004 | Lange | |
| 2002/0193856 A1* | 12/2002 | Lu | ............................. A61F 7/08 607/114 |
| 2004/0186541 A1 | 9/2004 | Agarwal et al. | |
| 2005/0056645 A1* | 3/2005 | Buckley | ................. B65D 51/18 220/257.1 |
| 2006/0157487 A1 | 7/2006 | Rosendahl et al. | |
| 2008/0119916 A1 | 5/2008 | Choucair et al. | |
| 2008/0255644 A1 | 10/2008 | Carson | |
| 2009/0048650 A1 | 2/2009 | Junkins | |
| 2009/0229593 A1 | 9/2009 | Komiya | |
| 2010/0010599 A1 | 1/2010 | Chen et al. | |
| 2011/0204065 A1 | 8/2011 | Kolowich | |
| 2012/0305231 A1 | 12/2012 | Liang et al. | |
| 2016/0346116 A1 | 12/2016 | Ohmer | |

FOREIGN PATENT DOCUMENTS

| | | |
|---|---|---|
| CN | 201179139 Y | 1/2009 |
| CN | 201647287 U | 11/2010 |
| CN | 201668583 U | 12/2010 |
| CN | 102512279 A | 6/2012 |
| CN | 203306402 U | 11/2013 |
| CN | 206606402 U | 11/2017 |
| DE | 187404 C | 12/1929 |
| DE | 552930 C | 6/1932 |
| DE | 55259 C | 12/1932 |
| DE | 511569 C | 3/1935 |
| DE | 1638820 U | 5/1952 |
| DE | 1645057 U | 10/1952 |
| DE | 1842006 U | 11/1961 |
| DE | 1906634 U | 12/1964 |
| DE | 19900197 C2 | 5/2001 |
| DE | 102014201887 A1 | 8/2015 |
| EP | 0960608 | 12/1999 |
| EP | 0960608 A2 | 12/1999 |
| EP | 1147992 A1 | 10/2001 |
| EP | 0960608 B1 | 1/2005 |
| EP | 2563302 B1 | 1/2017 |
| FR | 811526 * | 4/1937 |
| FR | 819762 | 10/1937 |
| GB | 160712 A | 3/1921 |
| GB | 157173 A | 12/1921 |
| GB | 225915 A | 12/1924 |
| GB | 245968 A | 1/1926 |
| GB | 246764 A | 2/1926 |
| GB | 304903 A | 1/1929 |
| GB | 385822 A | 1/1933 |
| GB | 496452 A | 11/1938 |
| GB | 604341 A | 7/1948 |
| GB | 1094364 A | 12/1967 |
| GB | 1227892 | 4/1971 |
| GB | 374495 * | 4/1981 |
| GB | 105735 A | 7/2003 |
| JP | S5324188 U | 3/1978 |
| JP | S6171111 U | 5/1986 |
| JP | H101312356 A | 12/1989 |
| JP | H063569 Y2 | 2/1994 |
| JP | 2003250679 A | 9/2003 |
| JP | 3141182 U | 4/2008 |
| JP | 3163042 U | 9/2010 |
| JP | 2011139757 A | 7/2011 |
| JP | 2013526917 A | 6/2013 |
| WO | WO2004026595 | 4/2004 |
| WO | 2007117159 A1 | 10/2007 |
| WO | 2009139877 A1 | 11/2009 |
| WO | 2012136535 A1 | 10/2012 |

OTHER PUBLICATIONS

Office Action from the Japanese Patent Office dated Jul. 16, 2019 in related Japanese application No. 2017-551014, and machine translation thereof.

Xavier Py, Regis Olives, Sylvain Mauran, Paraffin/porous-graphite-matrix composite as a high and constant power thermal storage material, International Journal of Heat and Mass Transfer, vol. 44, Issue 14, 2001, p. 2727-2737.

Communication from the German Patent Office dated Aug. 1, 2019 in related German application No. 20 2015 309 660, and translation thereof.

English translation of the International Search Report dated Sep. 15, 2016 for parent application No. PCT/EP2015/080681.

English translation of the Written Opinion dated Jun. 7, 2017 for parent application No. PCT/EP2015/080681.

Office Action dated Oct. 24, 2019 from the Chinese Patent Office in related Chinese application No. 201580069848.2, and machine translation of substantive portions thereof.

Decision of German Patent & Trademark Office dated Feb. 12, 2020 in counterpart DE utility model application No. 20 2015 009 660.3, with English summary attached thereto.

Examination Report of the European Patent Office dated May 25, 2020 in counterpart EP application 15823331, and machine translation thereof.

Excerpt from Fashy Catalog 1999/2000, pp. 1-3.

Excerpt from Fashy Catalog 2002/2003, pp. 30-31.

Office Action from the Chinese Patent Office dated Mar. 30, 2020 in related Chinese application No. 201580069848.2, and translation thereof.

Office Action from the Japanese Patent Office dated Apr. 21, 2020 in related Japanese application No. 2017-551014, and translation thereof.

Third Party Observation mailed by the EPO on Jan. 27, 2020 in counterpart EP application No. EP15823331, with English translation attached thereto.

* cited by examiner

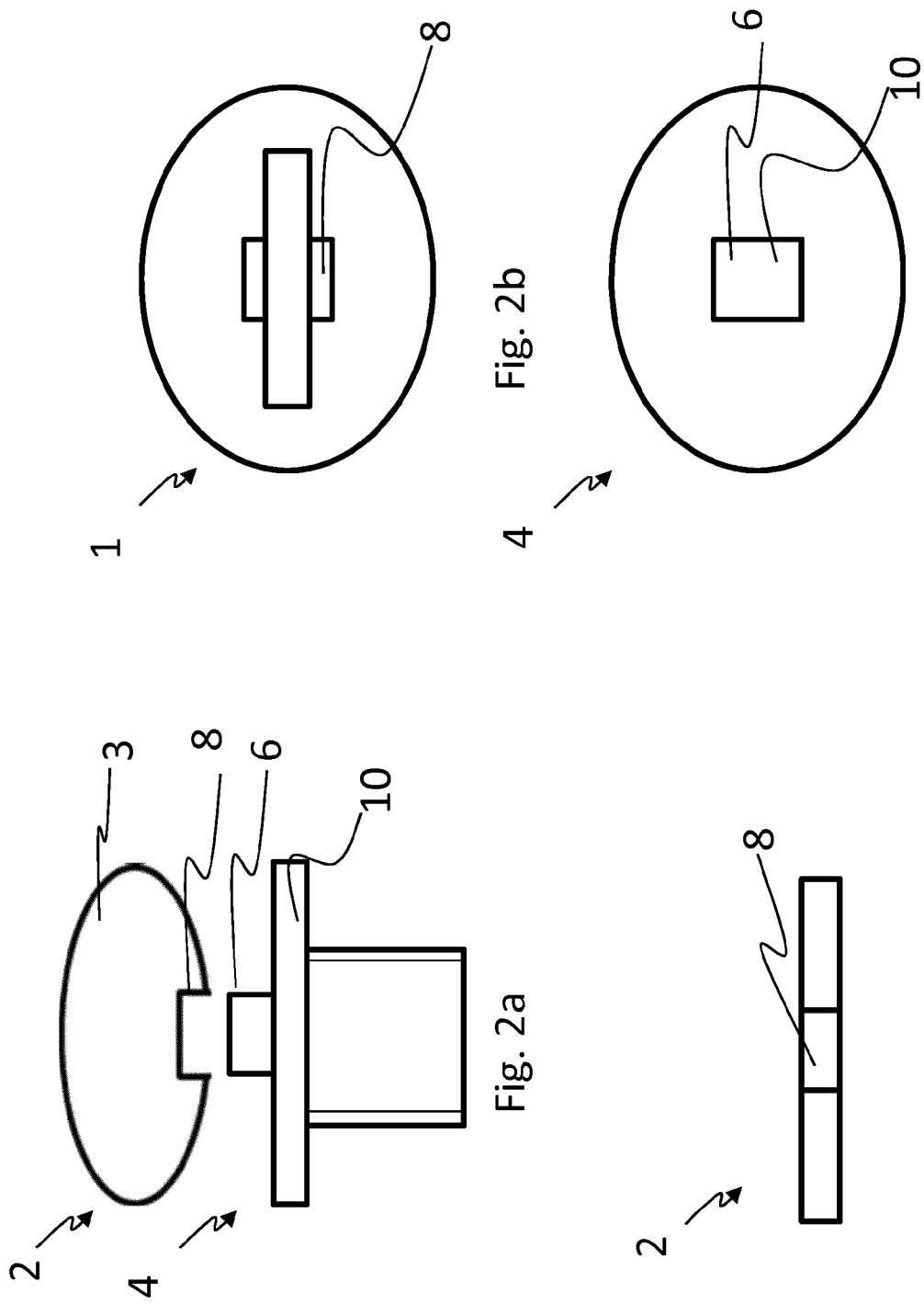

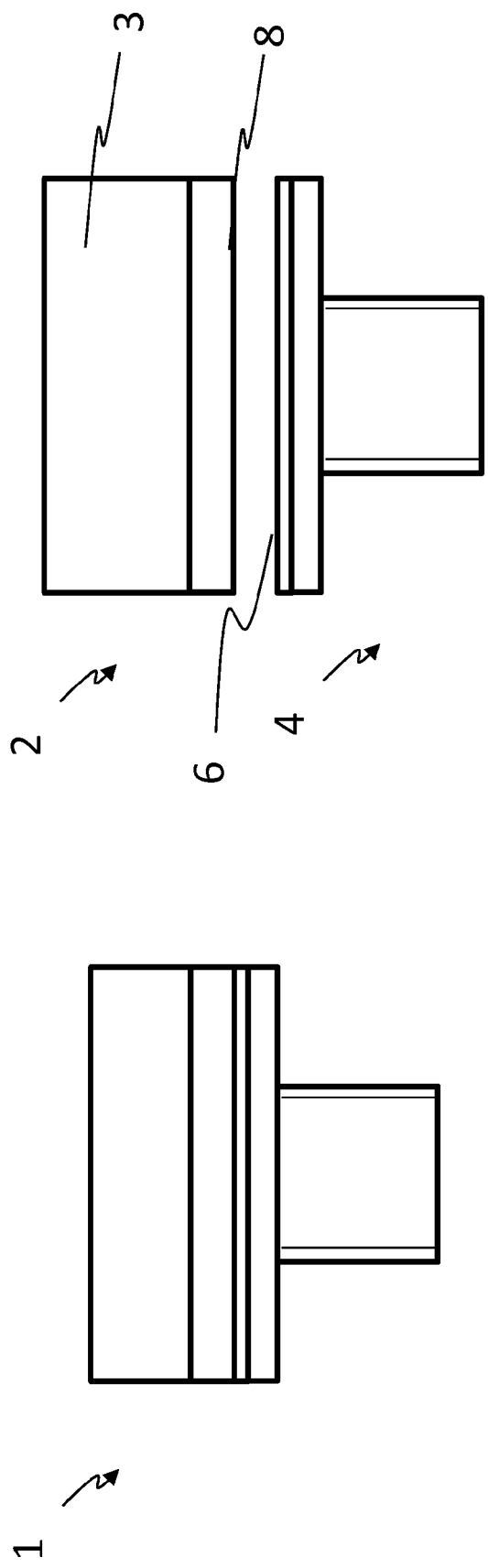

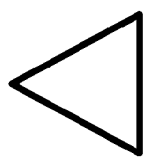
Fig. 5a
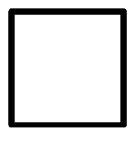
Fig. 5b
Fig. 5c
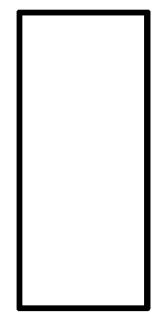
Fig. 5d
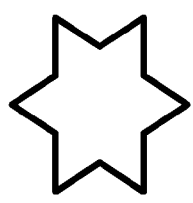
Fig. 5e
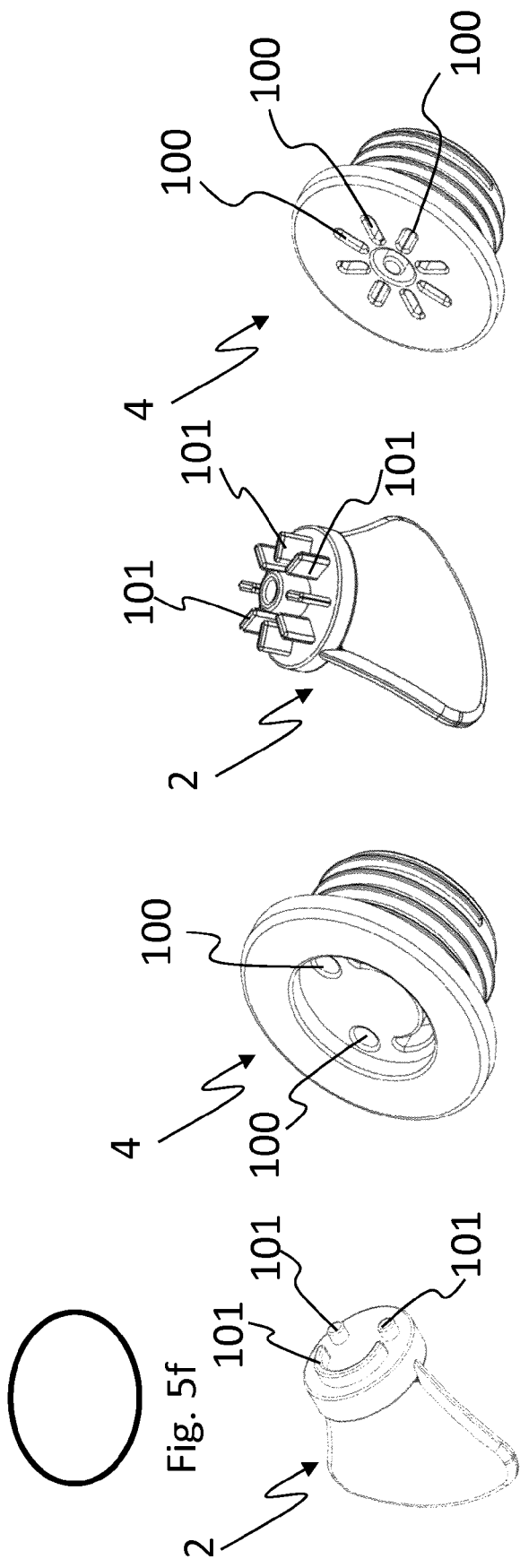
Fig. 5f   Fig. 5g   Fig. 5h
Fig. 5i   Fig. 5j

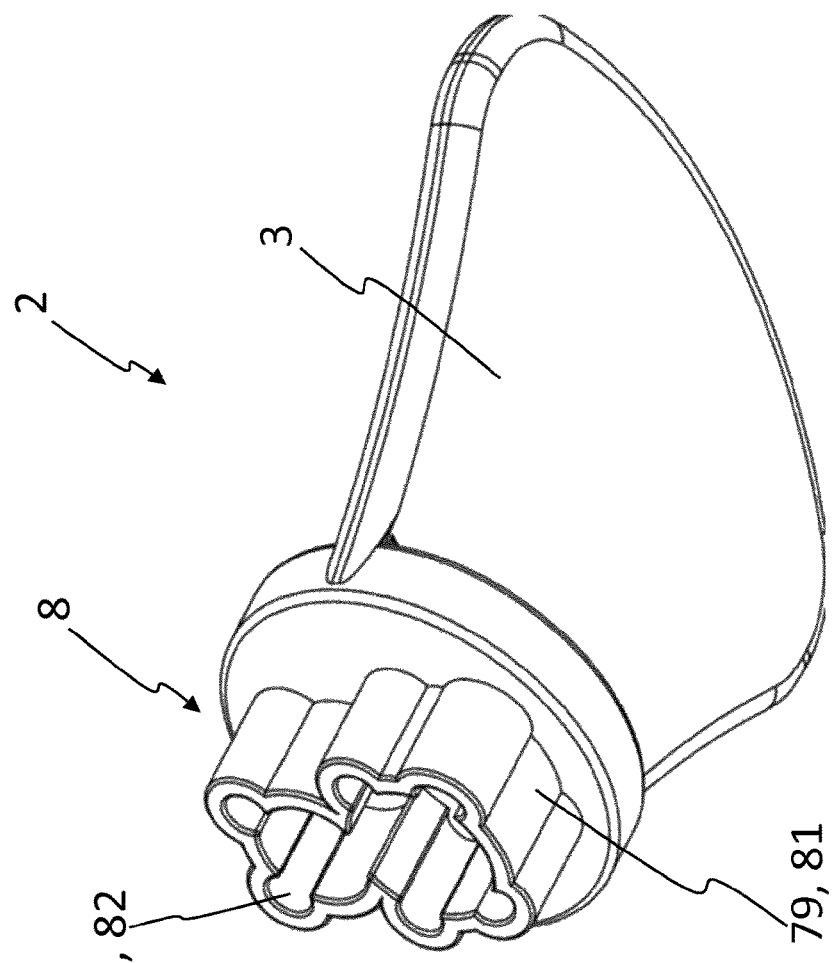
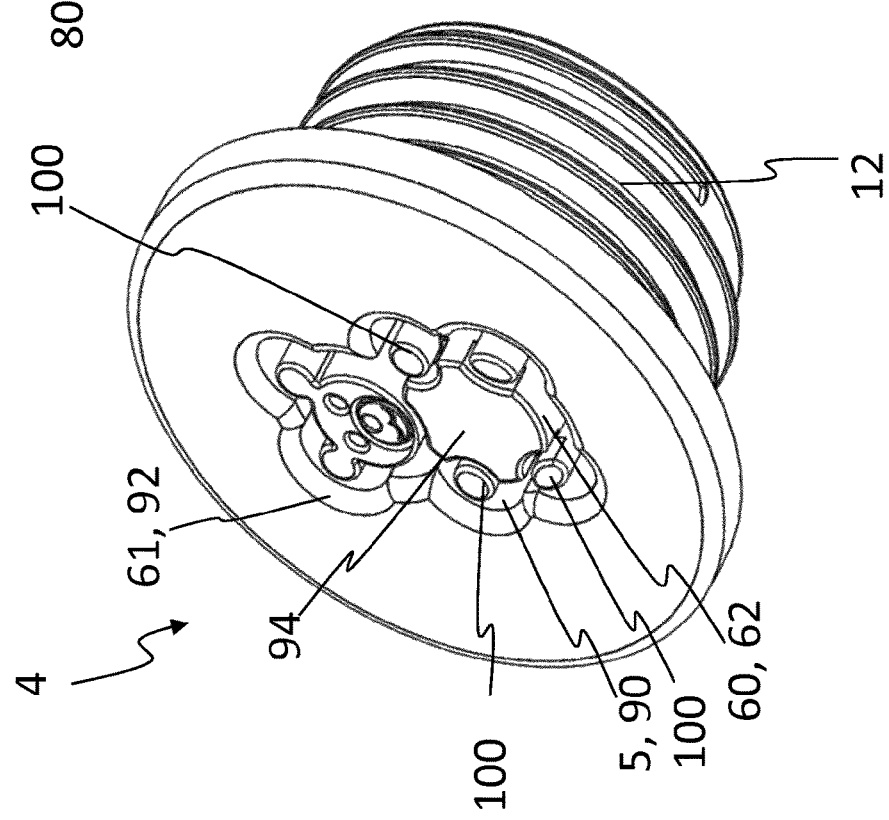

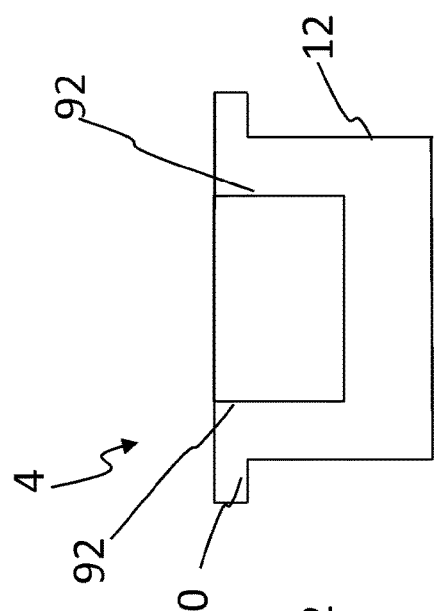
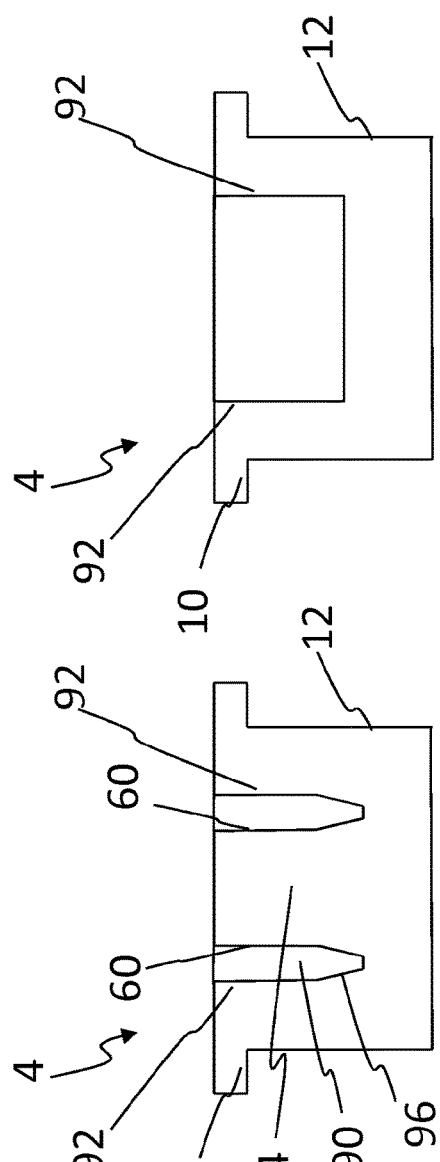
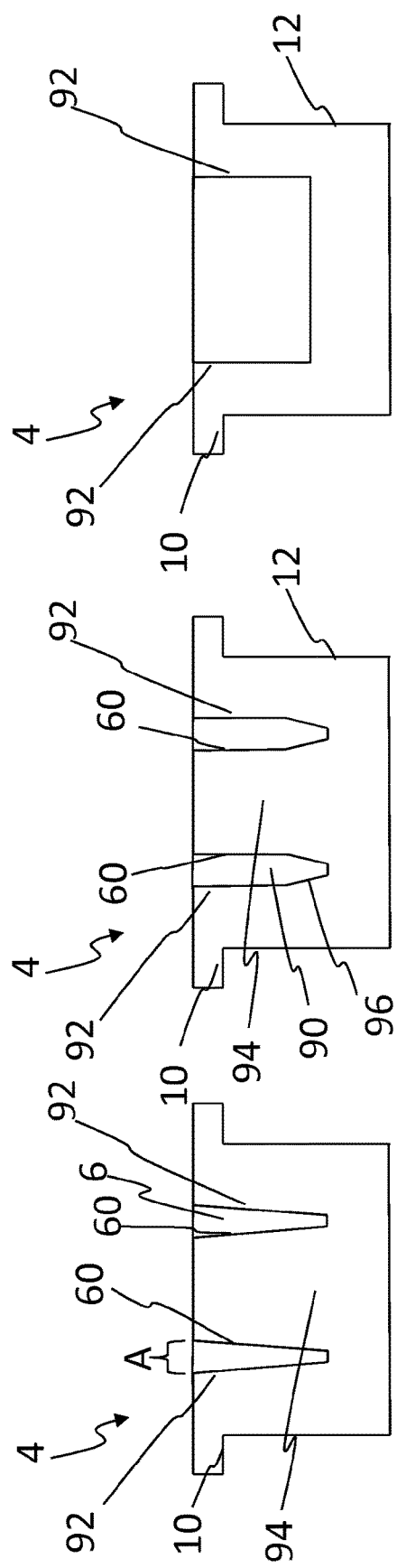
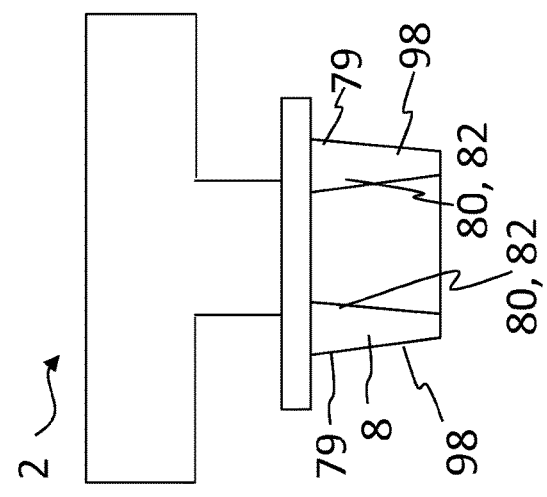
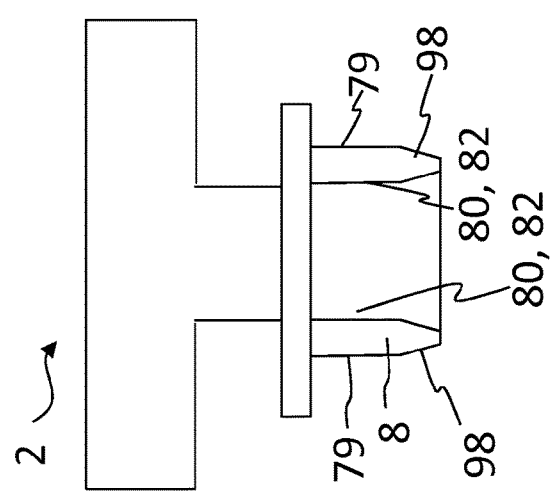
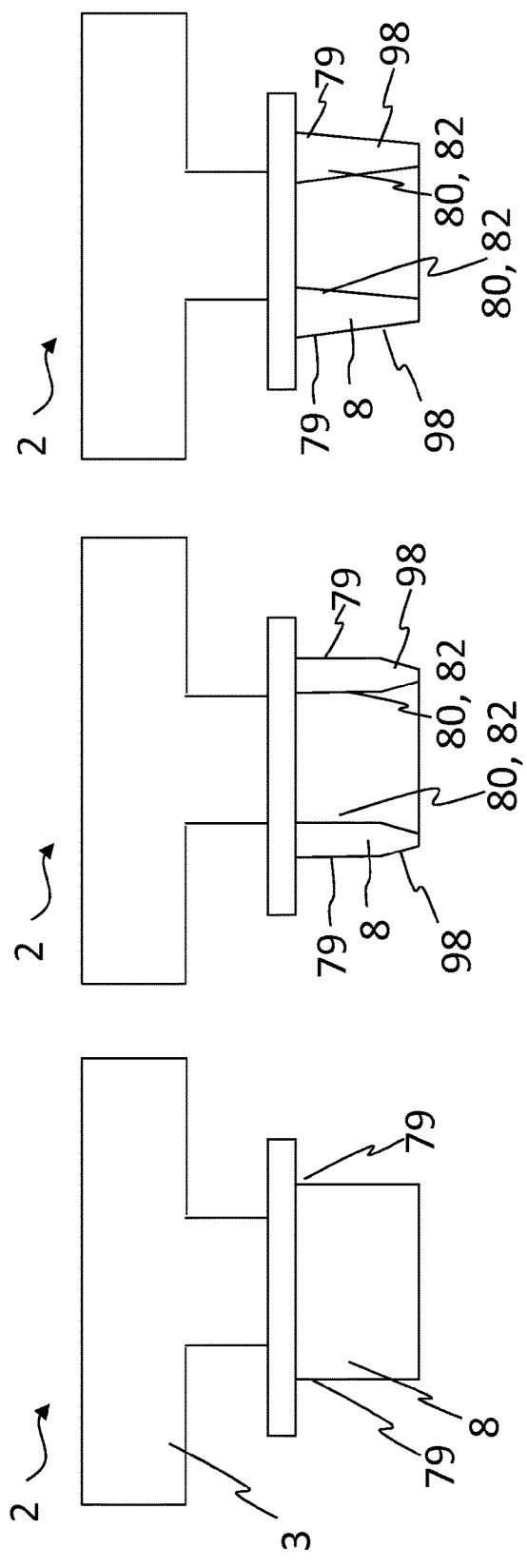

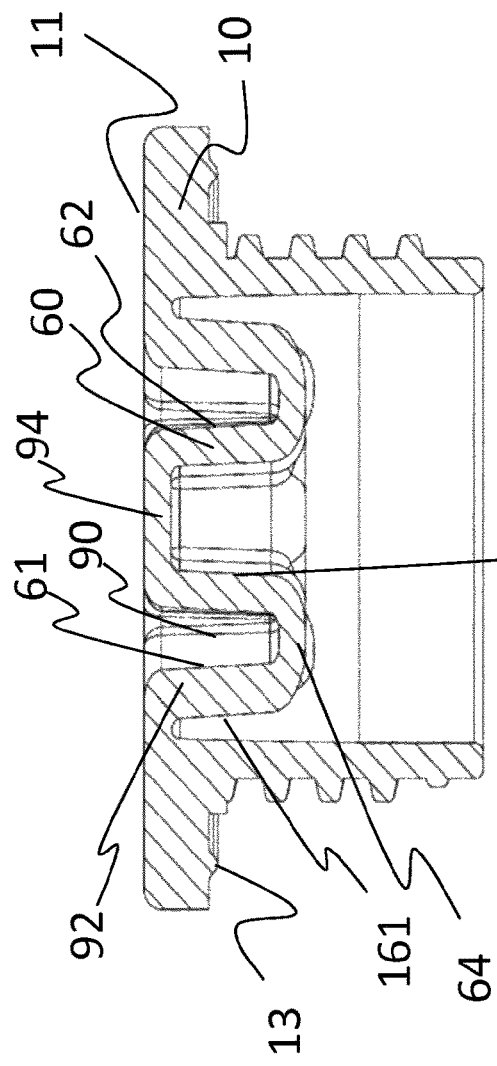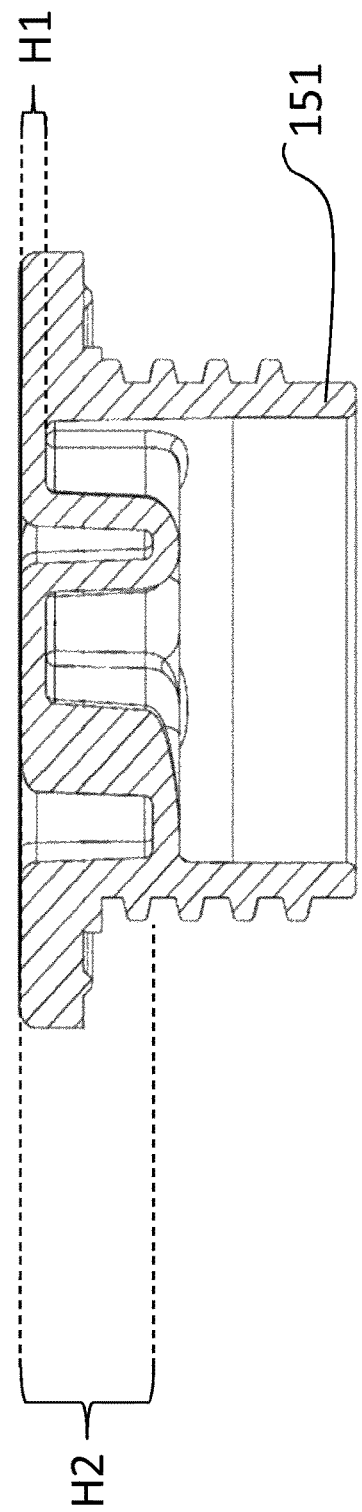

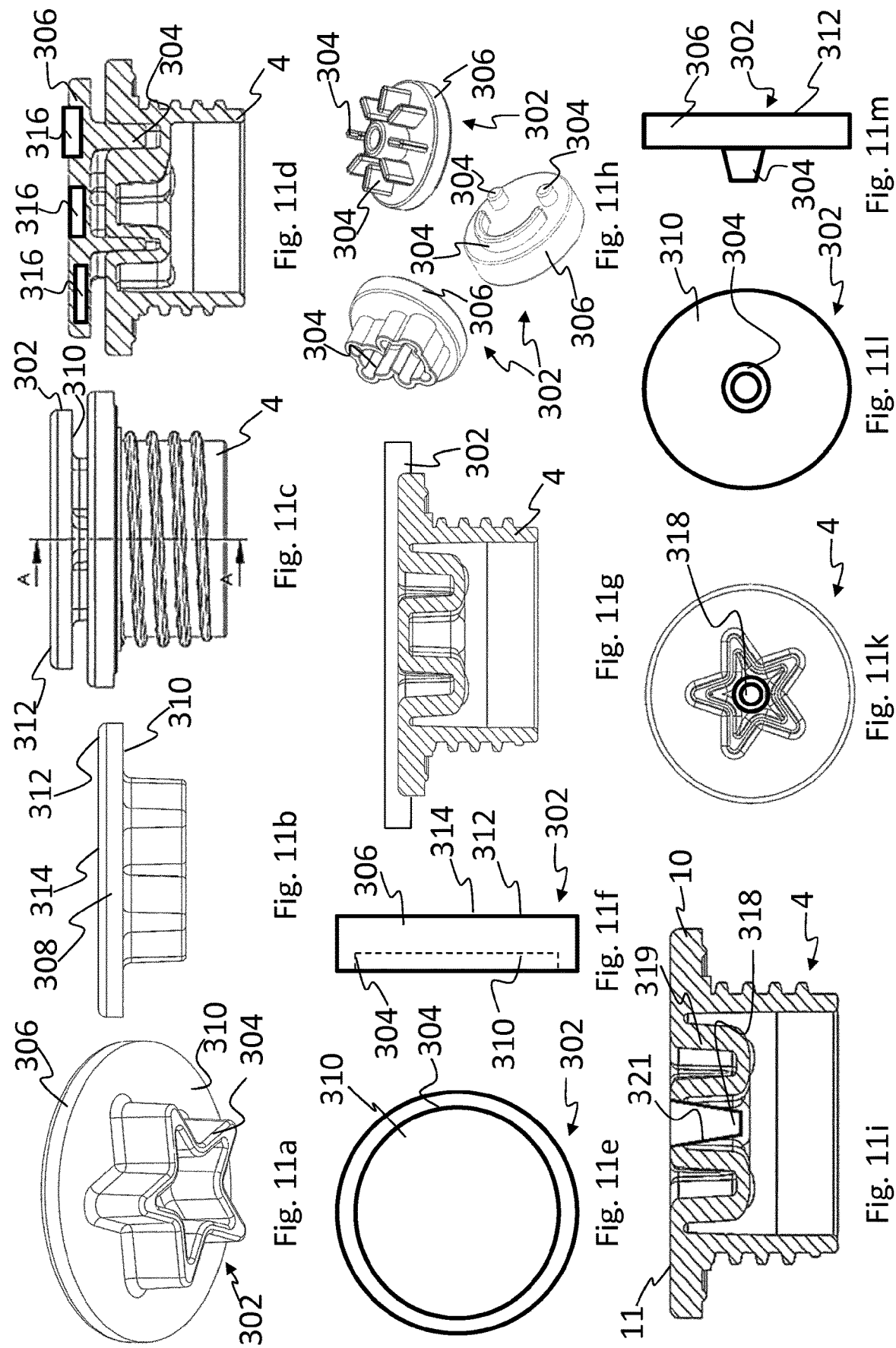

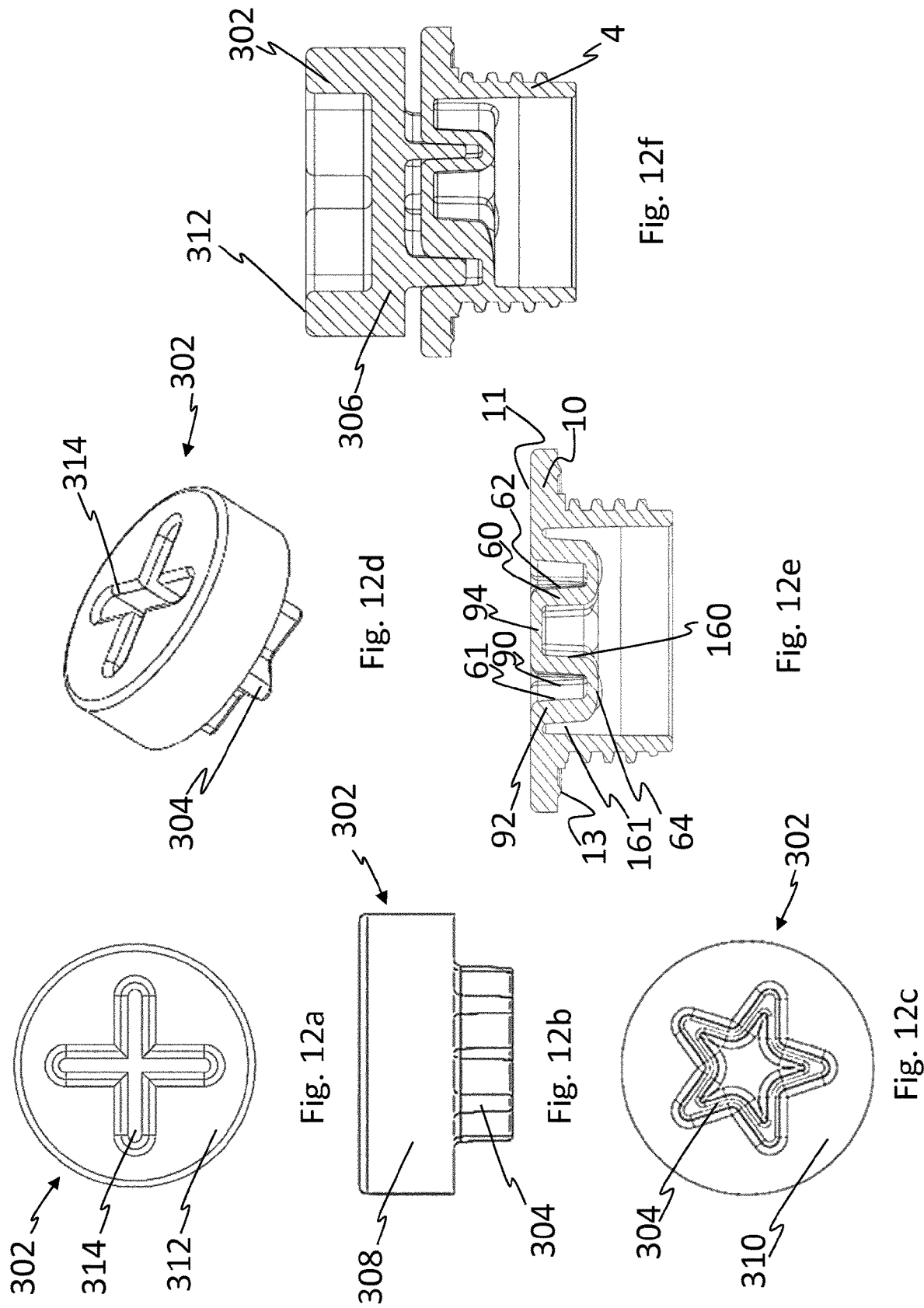

SAFETY CLOSURE FOR A HOT-WATER BOTTLE

The present invention relates to a safety closure for a hot-water bottle, and to a hot-water bottle having a safety closure.

The first hot-water bottles consisting of plastic or rubber have existed since the 1920s (http://de.wikipedia.org/wiki/W%C3% A4rmflasche#Geschichte). Since then, the product hot-water bottle has become so widespread that almost every household has one.

The prevalence of the hot-water bottle can be explained in that, e.g., it is suitable for a very large variety of applications and thus represents an enrichment for a very large number of people. For instance, hot-water bottles are used, e.g. in case of illness, discomfort or for the local tempering of body parts, in particular in the case of tensions. In addition, the heat provided by the hot-water bottle often has a calming effect.

On principle, hot-water bottles are thereby filled with very hot to boiling water, even though almost every hot-water bottle has a statement according to the British Standard BS 1970:2012, which points out that boiling water should not be added. Hot, in particular almost boiling water, can cause heavy scalding in contact with the skin of a human or an animal, which can cause permanent damages. In the case of an unintentional opening of the hot-water bottle, the water stored therein can escape and can thus scald the skin of a human or animal.

Hot-water bottles are a highly sophisticated mass-produced product, millions of which are sold every year, whereby it can already be concluded that significant resources have been and are being used for improving hot-water bottles. Furthermore, a very large number of industrial property rights have already been published, which reflects the intensive discussion of the object "hot-water bottle". E.g., publications GB230731A and EP0960608A2 thus disclose devices for more easily opening closed hot-water bottles, A further device is thereby arranged above the closure for the hot-water bottle. The further device thereby represents a lever element, by means of which an extension of the lever arm acting on the closure is formed, whereby the forces required for opening the hot-water bottle decrease by means of the lever arm extension with the increasing lever arm. In EP0960608A2, the opinion is expressed that the force required for opening a closure for a hot-water bottle increases as the hot-water bottle cools down. However, this also means that a hot-water bottle, which has only recently been filled with hot water and which has cooled down only insignificantly, can be opened easily. On principle, publications GB230731A and EP0960608A2 disclose the use of common closures. Due to the fact that the used closures are standard closures, a child or a person with dementia cannot unintentionally open the hot-water bottle, which is filled with hot water, by applying a force to the element for the manual contacting arranged on the closure. Publications DE19900197C2, DE 1906634U, DE 1842006U, DE 1645057U, DE 1638820U, DE 611569A, DE 552591A, DE552930A, DE487404A, GB157173, WO2012/136535A1, GB496452, GB105735, GB160712, GB225915, GB 227345, GB245968, GB246764, GB304903, GB604341, GB385822, GB1094364 further disclose closures for hot-water bottles, by means of which the safety or the comfort in the use of a hot-water bottle is to be increased.

Nonetheless, none of the above-mentioned subject matters was able to provide a solution, based on which burns caused by the use of a hot-water bottle are reduced. With regard to the use of hot-water bottles, it can thus be gathered from the homepage www.paulinchen.de—an initiative for children with burn injuries: "Only fill the hot-water bottle with water below 50° Celsius and close it well" (see http://www.paulinchen.de/fileadmin.content/2012_Downdloads/Gefahren-in_Kueche_und_Bad.pdf, downloaded on Dec. 18, 2014). As is well-known, "close well" is always understood as a closing using a large force. Children, who play, or persons with dementia, however, can activate such closures unintentionally or by chance and can thus remove the closure, whereby the hot water can escape from the hot-water bottle. Due to the large opening diameter of more than 16 mm, in particular of more than 18 mm, the water, which is filled into a hot-water bottle, can escape very quickly from the hot-water bottle, whereby significant body surface area parts of the person using the hot-water bottle, can be injured or scalded, respectively, very quickly.

A trend towards increasingly large elements for the manual contacting can furthermore be seen. The increasing size of the elements for a manual contacting thereby supports a low-force, water-tight closing of the hot-water bottle and a low-force opening of the hot-water bottle. The elements for manually contacting hot-water bottles have widths of more than 3 cm or of more than 4 cm or of more than 4.5 cm.

Due to the fact that hot-water bottles are also handed to children or persons with dementia, there is thus the risk that these persons open the freshly-filled hot-water bottle and get scalded by the water, which escapes. In particular persons suffering from dementia, can often apply large forces or remember the function of the closure for the hot-water bottle, and then actuate it.

It is thus the object of the invention at hand to provide a safety closure for a hot-water bottle, which solves the above-mentioned problem or which provides an effective alternative, respectively, for the known closures.

The above object is solved according to the invention by means of a multi-part safety closure for a hot-water bottle, in particular for preventing an unauthorized opening of a hot-water bottle by third parties, according to claim 1. The safety closure for hot-water bottles comprises at least one closure part having an external screw thread for screwing into an internal screw thread of a hot-water bottle, and having a first force transmission element for transmitting momentum for screwing the closure part into an internal screw thread of a hot-water bottle for sealing the hot-water bottle in a water-tight manner and for unscrewing the closure part from an internal screw thread of a hot-water bottle; and a manual actuating element having a second force transmission element for introducing the momentum required to screw and unscrew the closure part into and from an internal screw thread of a hot-water bottle into the closure part, wherein the first force transmission element and the second force transmission element are embodied to correspond or negatively to one another in such a way that the closure part and the manual actuating element can be releasably coupled to one another by forming an operative connection, in particular a frictional connection and/or a positive connection and/or a magnetic connection.

In the alternative, the solution according to the invention is described by means of a multi-part safety closure for a hot-water bottle for preventing an unauthorized opening of the hot-water bottle by third parties, wherein a closure part for the water-tight sealing of a hot-water bottle is designed, and a further manual actuating element, which can be releasably coupled to the closure part, for screwing the closure part into the hot-water bottle is designed, whereby only the manual actuating element has a positive connection area, in particular a lever, for manually introducing the torques required for opening and water-right sealing of the closure for the hot-water bottle.

The safety closure for the hot-water bottle according to the invention has the advantage that hot-water bottles, which are closed therewith, can also be handed to groups of people, who cannot foresee the dangers of an uncontrolled opening, such as, e.g., children or persons suffering from dementia. This is so, because, due to the multi-part embodiment of the safety closure for a hot-water bottle according to the invention, the manual actuating element required for opening and closing, can be stored at a location, which these persons cannot access. The closure part can further also not be removed accidentally by "playing around", because the required application of force—in the case of correct closure—cannot be opened without an element, which corresponds to the first force transmission element.

Further preferred embodiments are the subject matter of the subclaims and of the following description.

A torque of at least 1.3 Nm and preferably of at least 1.4 Nm or of at least 1.5 Nm or of at least 1.6 Nm or of at least 1.7 Nm or of at least 1.8 Nm or of at least 1.9 Nm or of 2 Nm+/−0.1 Nm and preferably with maximally 2.5 Nm or maximally 2.6 Nm or maximally 2.7 Nm or maximally 2.8 Nm or maximally 2.9 Nm or maximally 3 Nm or maximally 3.5 Nm or maximally 4 Nm is to preferably be applied to the closure part for a water-tight sealing of a hot-water bottle or for screwing into a hot-water bottle, respectively.

According to a further preferred embodiment of the invention at hand, the first force transmission element is embodied as internal force transmission element and is embodied by surrounding wall portions, wherein the second force transmission element is embodied for at least sectionally penetrating the internal force transmission element or a penetration area of the closure part, respectively, or the first force transmission element is embodied as flat force transmission element, in particular having a hook-and-loop fastener.

According to a further preferred embodiment of the invention at hand, the first force transmission element is embodied as protruding force transmission element, whereby the protruding force transmission element preferably protrudes maximally 3 cm, in particular maximally 2.9 cm or 2.8 cm or 2.7 cm or 2.6 cm or 2.5 cm or 2.4 cm or 2.3 cm or 2.2 cm or 2.1 cm or 2.0 cm or 1.9 cm or 1.8 cm or 1.7 cm or 1.6 cm or 1.5 cm or 1.4 cm or 1.3 cm or 1.2 cm or 1.1 cm or 1.0 cm or 0.9 cm or 0.8 cm or 0.7 cm or 0.6 cm or 0.5 cm beyond the adjacent end of the thread and/or preferably has a maximum width of 2.9 cm, in particular of 2.8 cm or 2.7 cm or 2.6 cm or 2.5 cm or 2.4 cm or 2.3 cm or 2.2 cm or 2.1 cm or 2.0 cm or 1.9 cm or 1.8 cm or 1.7 cm or 1.6 cm or 1.5 cm or 1.4 cm or 1.3 cm or 1.2 cm or 1.1 cm or 1.0 cm or 0.9 cm or 0.8 cm or 0.7 cm.

Particularly preferably, the first force transmission element is embodied as protruding force transmission element, wherein a lever arm for introducing the torque for opening and closing a hot-water bottle is embodied by means of the protruding force transmission element, wherein the lever arm is shorter than a lever arm, which is embodied by the manual actuating element, for introducing the torque for opening and closing a hot-water bottle. This embodiment is advantageous, because a shape, which does not provide for a manual opening of the hot-water bottle without the manual actuating element, is provided in any event. The lever arm of the manual actuating element is preferably many times, in particular at least twice or at least three-times or at least four-times or at least five-times or at least six-times or at least seven-times or at least eight-times or at least nine-times or at least ten-times or at least eleven-times or at least twelve-times or at least fifteen-times or at least twenty-times larger than the lever arm of the closure part. Particularly preferably, the protruding force transmission element has one or a plurality of lever arms, wherein the maximum length of a lever arm or of each lever arm is 2 cm, in particular 1.9 cm or 1.8 cm or 1.7 cm or 1.6 cm or 1.5 cm or 1.4 cm or 1.3 cm or 1.2 cm or 1.1 cm or 1.0 cm or 0.9 cm or 0.8 cm or 0.7 cm or 0.5 cm or 0.4 cm.

According to a further preferred embodiment of the invention at hand, the coupling between manual actuating element and the closure part can at least be released or can preferably only be released, when the closure part for closing a hot-water bottle is screwed into the internal screw thread of the hot-water bottle. The manual actuating element and the closure part can be moved freely or arbitrarily to one another, respectively, in an uncoupled state.

According to a further preferred embodiment of the invention at hand, the closure part has an at least sectionally and preferably completely circumferential collar, wherein the collar serves as stop for delimiting the maximum screw-in depth and/or as sealing element. Preferably, a seal is arranged or embodied in or on the collar. Preferably, the sealing element is embodied as a circumferential sealing element, wherein the circumferential sealing element is preferably embodied as an elevation having a curved contact surface and particularly preferably is a one-piece part of the collar and thus of the closure part.

According to a further preferred embodiment of the invention at hand, the closure part and/or the manual actuating element are injection molded parts, which preferably consist of a polymer material, wherein the polymer material has a temperature stability of at least 100° C. and preferably of at least 120° C. or of at least 150° C. (preferably up to 200° or up to 300° C. or up to 500° C. or up to 800° C.)

According to a further preferred embodiment of the invention at hand, the closure part is embodied for closing hot-water bottle openings, which have an opening diameter of at least 16 mm or of at least 17 mm or of at least 18 mm or of at least 19 mm or of at least 20 mm (preferably up to 30 mm or up to 40 mm or up to 50 mm).

The invention further refers to a manual actuating element for use in a safety closure for a hot-water bottle according to claim 1. The manual actuating element thereby preferably comprises at least one force transmission element for introducing the momentum required to screw and unscrew the closure part into and from an internal screw thread of a hot-water bottle in the closure part.

The invention further relates to a closure part for use in a safety closure for a hot-water bottle according to claim 1. The closure part thereby preferably comprises at least one external screw thread for screwing into an internal screw thread of a hot-water bottle, and a force transmission element for transmitting momentum for screwing the closure part into an internal screw tread of a hot-water bottle for the water-tight sealing of the hot-water bottle and for unscrewing the closure part from the internal screw thread of a hot-water bottle.

According to a further preferred embodiment of the invention at hand, at least a part of a penetration area of the closure part, into which the second force transmission element can be introduced, is delimited by means of a wall, which at least sectionally and preferably mostly and particularly preferably completely encloses the penetration area. At least sections of the second force transmission element thereby preferably have an exterior wall, which is capable of being coupled to the enclosing wall of the penetration area. Being capable of being coupled thereby preferably means capable of being contacted, in particular capable of being contacted to transmit forces. In addition to the enclosing wall, the penetration area is alternatively preferably also delimited by means of at least one outer wall by at least one elevation, which is embodied in the area, which is delimited by the enclosing wall, in particular a pin-like or column-like element. The elevation is thus preferably arranged in an area, which is at least partially and preferably mostly and particularly preferably completely surrounded or enclosed, respectively, by the enclosing wall.

According to a further preferred embodiment of the invention at hand, the force transmission element is embodied as internal force transmission element and is preferably embodied completely or partially by surrounding wall portions or the force transmission element is embodied as flat force transmission element, it in particular preferably has a hook-and-loop fastener, or the force transmission element is embodied as protruding force transmission element, wherein the protruding force transmission element protrudes maximally 3 cm, in particular maximally 2.9 cm or 2.8 cm or 2.7 cm or 2.6 cm or 2.5 cm or 2.4 cm or 2.3 cm or 2.2 cm or 2.1 cm or 2.0 cm or 1.9 cm or 1.8 cm or 1.7 cm or 1.6 cm or 1.5 cm or 1.4 cm or 1.3 cm or 1.2 cm or 1.1 cm or 1.0 cm or 0.9 cm or 0.8 cm or 0.7 cm or 0.6 cm or 0.5 cm beyond the adjacent end of the thread and/or has a maximum width of 2.0 cm, in particular of 1.9 cm or 1.8 cm or 1.7 cm or 1.6 cm or 1.5 cm or 1.4 cm or 1.3 cm or 1.2 cm or 1.1 cm or 1.0 cm or 0.9 cm or 0.8 cm or 0.7 cm.

According to a further preferred embodiment of the invention at hand, the first force transmission element and the second force transmission element are designed so as to correspond, wherein, to establish the operative connection, the first force transmission element and the second force transmission element can be brought into contact with one another in such a way that the corresponding portions of the first force transmission element and of the second force transmission element come into contact with one another, wherein the corresponding portions are embodied so as to be curved at least sectionally, in particular mostly by area or completely. This solution is particularly advantageous, because—without the corresponding force transmission element—the closure portion can be transferred manually or with further aids only with great difficulty from a state, which seals a hot-water bottle, into a state, which does not seal a hot-water bottle due to rounded surfaces.

According to a further preferred embodiment of the invention at hand, the protruding or pin-like force transmission element, respectively, in particular protruding in the longitudinal direction of the closure part, beyond the collar surface, of the closure part is designed in such a way that the introduction of a torque of 2 Nm+/−0.1 Nm into the closure part for the water-tight sealing and for opening a hot-water bottle requires an application of force to the protruding force transmission element with a force of more than 50 N, in particular of more than 55 N or of more than 60 N or of more than 65 N or of more than 60 N or of more than 65 N or of more than 70 N or of more than 75 N or of more than 80 N or of more than 85 N or of more than 90 N or of more than 95 N or of more than 100 N or of more than 105 N or of more than 110 N or of more than 115 N or of more than 120 N or of more than 125 N or of more than 130 N or of more than 140 N or of more than 150 N or of more than 160 N or of more than 170 N or of more than 180 N or of more than 190 N or of more than 200 N or of more than 210 N or of more than 220 N or of more than 230 N or of more than 240 N or of more than 250 N or of more than 260 N or of more than 270 N or of more than 280 N or of more than 290 N or of more than 300 N or of more than 310 N or of more than 320 N or of more than 330 N or of more than 340 N or of more than 350 N. This solution is advantageous, because the closure element can be embodied in particular in a target-group dependent manner in such a way that the forces, which can be applied by the individual persons of the target group, are smaller than those for opening a hot-water bottle, which is closed by means of the safety closure for a hot-water bottle according to the invention. It is further possible for the force, which is to be introduced into the closure part via the protruding force transmission means, to be so large that it cannot be opened by more than 90%, in particular by more than 99%, of the persons of this target group, in particular children and persons with dementia.

In another aspect of the present teachings, a kit includes a multi-part safety closure for a hot-water bottle or at least one manual actuating element and at least one hot-water bottle closure part 11 and preferably a closure part attachment element and a hot-water bottle having a filling opening and a thread arranged in an area of the filling opening for coupling to the safety closure for a hot-water bottle and preferably having a cover, which can be arranged around the hot-water bottle, preferably for at least partially insulating the hot-water bottle or for at least partially reducing, respectively, the heat transport from the hot-water bottle to the user.

In another aspect of the present teachings, a computer program product comprises a digital description of the form of the manual actuating element and/or of the closure part or of the safety closure for a hot-water, wherein the digital description can be used to control a 3D printer, or a closure part attachment element.

In another aspect of the present teachings, a production method is disclosed for producing the manual actuating element and/or the closure part or the safety closure part for a hot-water bottle and/or a closure part attachment element. Such a production method preferably comprises at least the steps of: providing form data relating to the closure part and/or to the manual actuating element or to the safety closure for a hot-water bottle, uploading the form data into a control device for controlling a 3D printer, and printing the closure part and/or the manual actuating element or the safety closure for a hot-water bottle.

The invention can further relate to a multi-part safety closure for a hot-water bottle, which preferably comprises at least:

A closure part having an external screw thread for screwing into an internal screw thread of a hot-water bottle and having a first force transmission element for transmitting momentum for screwing the closure part into an internal screw thread of a hot-water bottle for sealing the hot-water bottle in a water-tight manner and for unscrewing the closure part from an internal screw thread of a hot-water bottle, and a manual actuating element having a second force transmission element for introducing the momentum required to screw and unscrew the closure part into and from an internal screw thread of a hot-water bottle into the closure part, at least one closure part attachment element, in particular an intermediate member or adapter, for the releasable arrangement between the manual actuating element and the closure part is provided, wherein the closure part attachment element is embodied so as to correspond with the first force transmission element on the one hand and so as to correspond with the second force transmission element on the other hand, wherein a momentum introduced via the manual actuating element can be introduced via the second force transmission element into the closure part attachment element and via the latter into the closure part.

According to a further preferred embodiment of the invention at hand, the closure part and the manual actuating element cooperate, in particular in a clamping manner, in such a way that the first force transmission element and the second force transmission element are held in a coupled state by the cooperation of the first force transmission element and the second force transmission element. This embodiment is advantageous, because the clamping can create a connection between the manual actuating element and the closure part, by means of which the closure part remains on the manual actuating element, when it is unscrewed from the thread. It goes without saying that the closure part can still be removed from the manual actuating element, but the hot-water bottle can be opened more easily because of the embodiment and the safety closure for a hot-water bottle can be stowed as a coupled assembly. At least sectionally, the penetration area of the closure part is preferably designed not to be as broad as the second force transmission element of the manual actuating element, which penetrates into the penetration area, from which a press fit or clamping respectively, can be created in response to introducing the second force transmission element into the penetration area.

According to a further preferred embodiment of the invention at hand, at least a section of the second force transmission element has an exterior wall, which can be coupled to the enclosing wall of the penetration area, whereby, in addition to the enclosing wall, the penetration area is preferably also enclosed by means of at least one outer wall by at least one elevation, in particular a pin-like or column-like element, which is embodied in the area delimited by the enclosing wall. The penetration area thus preferably has a trench-like design. In addition or in the alternative, it is possible that the penetration area is embodied as a plurality of partial penetration areas, which are spaced apart from one another and which can have, e.g., a blind hole-like design. It is further possible for sections of the penetration area to be embodied in a trench-like manner and that sections are embodied by means of a partial penetration area or a plurality of partial penetration areas. Partial force transmission elements of the closure part are preferably formed by the walls, by means of which the penetration area and/or the partial penetration areas are delimited.

The invention at hand further relates to a closure part attachment element for the releasable, in particular positive or frictional or magnetic field coupling with hot-water bottle closure part of the safety closure for a hot-water bottle according to the invention. The closure part attachment element thereby preferably comprises at least one positioning element or a plurality of positioning elements for arrangement on the hot-water bottle closure part. The closure part attachment element preferably further has at least one functional means, wherein the functional means preferably forms a functional area, wherein the functional area is preferably embodied for at least sectionally overlapping the force transmission element of the hot-water bottle closure part. The positioning element is preferably arranged or embodied on a first side or on a first side of the functional means or the positioning elements are arranged or embodied on a first side or on a first side of the functional means. In a state, in which the closure part attachment element is coupled to the hot-water bottle closure part, the functional means is preferably visible or touchable or accessible on a second side, which differs from the first side. In the state, in which the closure part attachment element is coupled to the hot-water bottle closure part, the first side of the functional means is preferably at least partially invisible or untouchable or inaccessible or covered. The functional means can hereby be embodied as electronic means, in particular as sensor means or can have one or a plurality of sensor means. Preferably, the sensor means are temperature sensors and/or brightness sensors or light sensors, respectively. In addition or in the alternative, the functional means can be embodied as coupling device for coupling one or a plurality of functional devices, such as, e.g. a sensor means or a light source, in particular a LED light source. Should the functional means be embodied as coupling device, is can be embodied for the positive, magnetic field, integral and/or frictional coupling. It is further possible for the coupling device to be embodied for the releasable or permanent coupling. It is further possible that the functional means has a coupling surface as coupling device, via which further devices, such as, e.g., an electronic means, can be arranged on the functional means. The closure part attachment element can furthermore have a battery for providing electrical energy for operating the electronic means. In addition or in the alternative, the electronic means can have a communication device, in particular a data transmission means, such as a radio interface, in particular a Bluetooth interface, for communicating with one or a plurality of further devices, in particular one or a plurality of processor devices, such as, e.g. one or a plurality of smart phone(s). The electronic means is preferably at least partially and preferably completely embedded into the structure of the closure part attachment element, in particular surrounded by the material, which mostly forms the closure part attachment element in terms of mass or in terms of volume. In the alternative, it is possible for the electronic means to be embedded in the structure of the closure part attachment element, which also forms the positioning element or the positioning elements.

The closure part attachment element can furthermore be embodied as a lid or cover. When it is embodied as lid or cover, the closure part attachment element preferably serves to thermally insulate the hot-water bottle closure part.

According to a further preferred embodiment of the invention at hand, the closure part attachment element can be provided for the releasable arrangement between the manual actuating element and the closure part, wherein the closure part attachment element is preferably embodied so as to correspond with the first force transmission element on the one hand and so as to correspond with the second force transmission element on the other hand, wherein a momentum introduced via the manual actuating element can be introduced via the second force transmission element into the closure part attachment element and via the latter into the closure part.

The invention at hand further relates to a lot. The lot thereby preferably comprises at least one packaging, in particular at least partially consisting of a polymer material, which delimits a receiving area, and a manual actuating element according to claim 10, which is enclosed in at least liquid-tight manner by the packaging in the receiving area and/or a hot-water bottle closure part according to claim 11 and/or a closure part attachment element according to claim 12 or a kit according to claim 13, which is enclosed in an at least liquid-tight manner by the packaging in the receiving area, wherein the entire receiving area, which is delimited by the packaging, is germ-reduced, in particular sterile.

In the context of the invention at hand, the term "sterile" is to preferably be understood in accordance with the standards EN 556-1 and EN 552, wherein the use is preferably directed to laboratory products and is particularly preferably directed to medical products. By reference, the standards EN 556-1 and EN552 are declared to be the subject matter of the document at hand in their entirety. Every state, which is reached by means of a treatment, which effects a reduction and/or inactivation of biomass, in particular active DNA or active DNA fragments or pathogens and/or microorganisms, in particular biologically active bacteria and/or biologically active viruses and/or biologically active spores, is hereby preferably understood as germ-reduced. The term germ-reduced thus preferably describes a state, which corresponds to the assurance level SAL 2 or at least to the assurance level SAL 2, in particular SAL 3 or at least SAL 3 or SAL 4 or at least SAL 4 or SAL 5. SAL hereby stands for the uniformly used term Sterility Assurance Level. In the context of the invention at hand, the term "sterile" thus preferably describes a state, which corresponds to the assurance level SAL 6 or higher.

According to a preferred embodiment of the invention at hand, at least one beam, in particular electron beam or gamma ray or UV light beam, created by a radiation source, in particular an electron accelerator, was applied to the lot, in particular the receiving area with the objects arranged therein, at least for reducing germs, in particular for sterilization, after introduction of the object and after sealing the packaging. The packaging can preferably not opened in a non-destructive manner.

In addition or in the alternative, it is possible hereby that a germ reduction, in particular sterilization, took place by means of applying gas to the packaging and to the object placed therein or of the objects, which are placed or which are to be placed therein, respectively. Preferably, the gas application is a functional gas application, in particular an ethylene oxide/EtO application. Particularly preferably, the packaging is already equipped with the object or the objects and is sealed in response to the gas application, wherein the packaging is preferably permeable for the respective functional gas.

The characteristics of the packaging and/or packaging materials are preferably specified in the standards DIN EN ISO 11607-1 and 11607-2 or DIN EN 868. By reference, these standards are made the subject matter of the document at hand in their entirety.

A negative or corresponding design hereby preferably identifies an embodiment in terms of a "key and a lock" or a plug and a socket for receiving the plug".

Individual or all illustrations of the figures described below are to preferably be considered to be design drawings, i.e. the dimensions, proportions, functional contexts and/or arrangements resulting from the figure or figures, respectively, preferably correspond exactly or preferably substantially to those of the device according to the invention or the product according to the invention, respectively.

Further advantages, goals and characteristics of the invention at hand will be described by means of the drawings attached to the following description, in which safety closures for a hot-water bottle according to the invention and their components are illustrated in an exemplary manner. Elements of the devices according to the invention, which at least substantially correspond in the figures with regard to their function, may hereby be identified with the same reference numerals, whereby these components or elements, respectively, do not need to be numbered or discussed in all figures. The invention will be described below merely in an exemplary manner by means of the enclosed figures.

The use of the words "substantially" defines a deviation in the range of 1%-30%, in particular of 1%-20%, in particular of 1%-10%, in particular of 1%-5%, in particular of 1%-2%, of the definition, which would be at hand without the use of these words, preferably in all cases, in which these words are used in the context of the invention at hand.

FIG. 2a shows a schematic side view of a second exemplary embodiment of a manual actuating element according to the invention and of a second closure part according to the invention in an uncoupled arrangement;

FIG. 2b shows a schematic top view onto a second exemplary embodiment of a multi-part safety closure for a hot-water bottle according to the invention;

FIG. 2c shows a schematic top view onto the underside of a second exemplary manual actuating element according to the invention;

FIG. 2d shows a schematic top view onto a second exemplary closure part according to the invention;

FIG. 3a shows a schematic side view of a third exemplary embodiment of a manual actuating element according to the invention and of a second closure part according to the invention in a coupled arrangement;

FIG. 3b shows a schematic side view of a third exemplary embodiment of a manual actuating element according to the invention and of a second closure part according to the invention in an uncoupled arrangement;

FIG. 3c shows a further schematic side view of the third exemplary manual actuating element according to the invention, wherein the manual actuating element is illustrated so as to be rotated by 90° as compared to the view shown in FIG. 3b;

FIG. 3d shows a schematic top view onto the third manual actuating element, which is illustrated in an exemplary manner, wherein the manual actuating element is oriented according to FIG. 3b;

FIGS. 5a-5j show different schematic illustrations of preferred cross sections of a force transmission element protruding from the manual actuating element according to the invention or from the closure part.

FIG. 7a shows a perspective illustration of a preferred closure part;

FIG. 7b shows a perspective illustration of a manual actuating element, which matches the closure part shown in FIG. 7a and FIGS. 8a-c show schematic cross sectional illustrations through closure parts according to the invention;

Figure 9B:
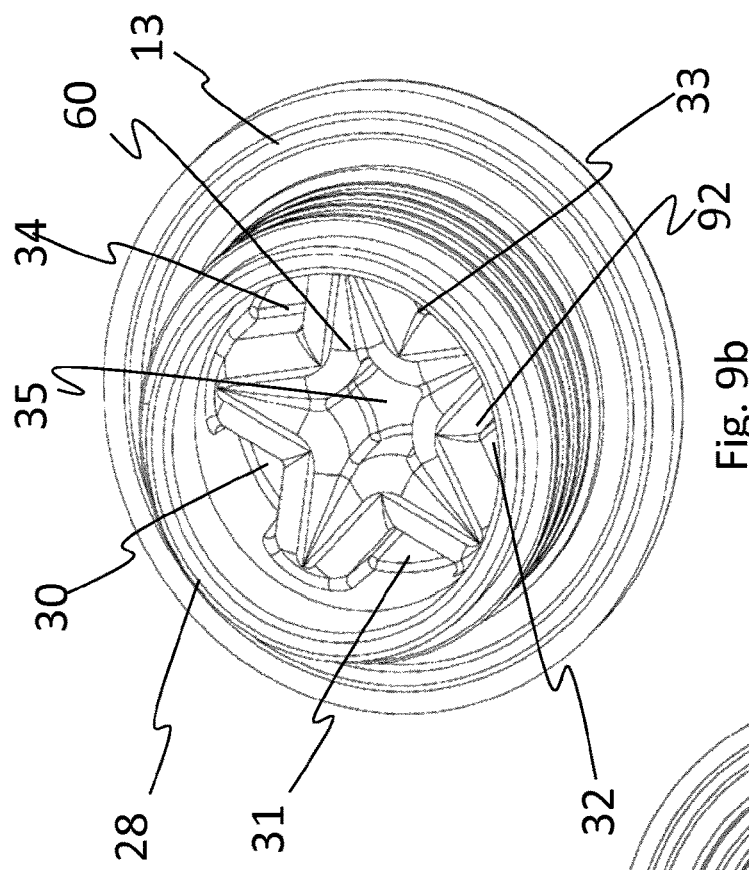
Figure 9A:
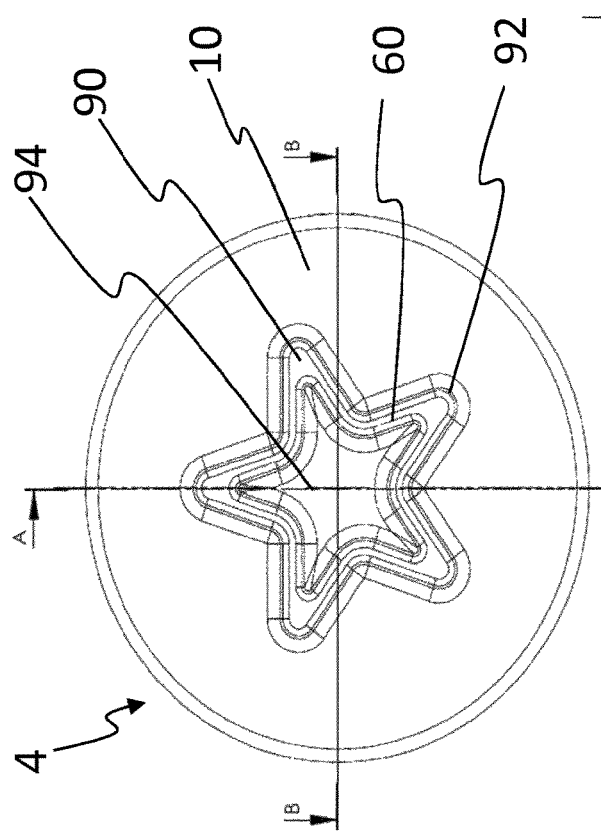
Figure 9C:
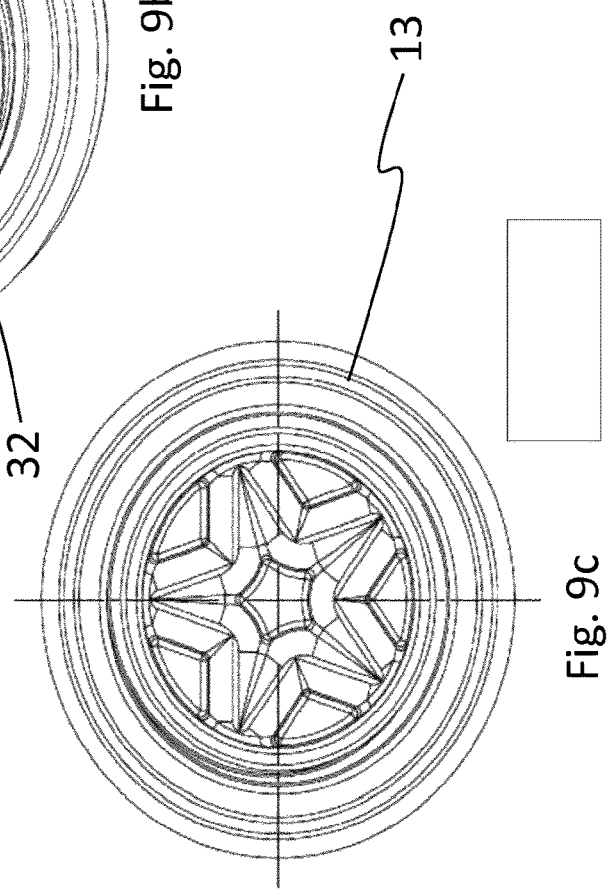

FIGS. 8*d-f* show schematic cross sectional illustrations through manual actuating elements according to the invention;

FIG. 9*a* shows a top view onto an example of a closure part according to the invention;

FIG. 9*b* shows a perspective bottom view of the closure part known from FIG. 9*a*;

FIG. 9*c* shows a bottom view of the closure part illustrated in perspective in FIG. 9*b*;

FIG. 10*a* shows a sectional illustration according to the section identified with B-B in FIG. 9*a*;

FIG. 10*b* shows a sectional illustration according to the section identified with A-A in FIG. 9*a*;

FIGS. 11*a-b* show two schematic and merely exemplary illustrations of a first embodiment of a closure part attachment element;

FIGS. 11*c-d* show two schematic and merely exemplary illustrations according to which the closure part attachment element from FIGS. 11*a-b* is coupled to a hot-water bottle closure part;

FIGS. 11*e-f* show two schematic and merely exemplary illustrations of a second embodiment of a closure part attachment element;

FIG. 11*g* shows a schematic and merely exemplary illustration according to which the closure part attachment element from FIGS. 11*e-f* is coupled to a hot-water bottle closure part;

FIG. 11*h* shows three schematic and merely exemplary illustrations of further possible embodiments of the closure part attachment element;

FIGS. 11*i-k* show two schematic and merely exemplary illustrations of a hot-water bottle closure with a central coupling location for coupling a closure part attachment element;

FIG. 11*l-m* show two schematic and merely exemplary illustrations of a further closure part attachment element, which is preferably embodied negatively to the coupling location of the hot-water bottle closure part shown in FIGS. 11*i-k*, preferably at least in the area of a coupling pin FIG. 12*a* shows a schematic and merely exemplary illustration of a top view onto a closure part attachment element, which is embodied as adapter or intermediate member, respectively;

FIG. 12*b* shows a schematic and merely exemplary illustration of a side view of the closure part attachment element shown in FIG. 12*a*;

FIG. 12*c* shows a schematic and merely exemplary illustration of a view from the bottom of the closure part attachment element shown in FIG. 12*a*;

FIG. 12*d* shows a schematic and merely exemplary perspective illustration of an illustration of the closure part attachment element shown in FIGS. 12*a-c*;

FIG. 12*e* shows an exemplary sectional illustration of a hot-water bottle closure part;

FIG. 12*f* shows an exemplary sectional illustration of the closure part attachment element shown in FIG. 12*d* and of the hot-water bottle closure part shown in FIG. 12*e*, in a coupled arrangement; and FIGS. 13*a-d* show different lots, wherein each lot includes a packaging and an object according to the invention, which is stored or arranged, respectively, in the packaging at least in a germ-reduced manner.

Figure 1A:
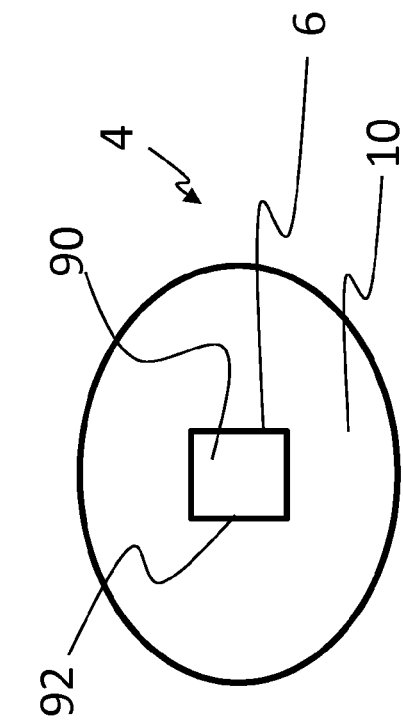
FIG. 1a shows a schematic side view of a first exemplary embodiment of a manual actuating element according to the invention.
Figure 1B:
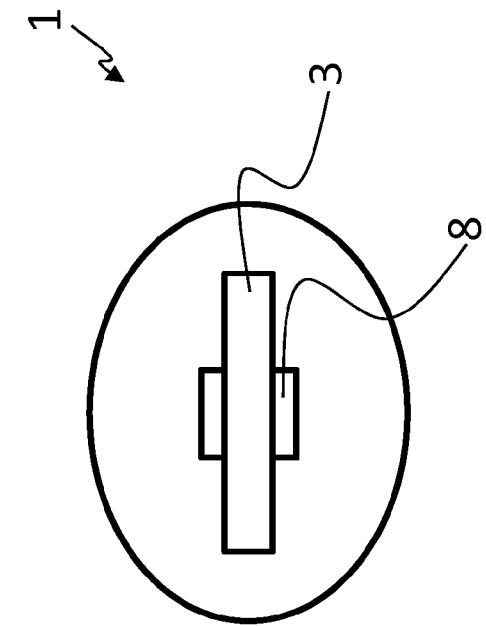
FIG. 1b shows a schematic top view onto a first exemplary embodiment of a closure part according to the invention.

FIG. 1*a* shows a manual actuating element 2. The shape of the element for manually contacting and force introduction 3 is hereby illustrated as an oval, but can also be round, rectangular or in any other shape. Reference numeral 8 identifies the second coupling element, which is embodied in a pin-like manner in the illustrated embodiment. Examples for the cross sectional shape of the pin-like second coupling element 8 are shown in FIGS. 5*a* to 5*f*. The cross sections shown by FIGS. 5*a* to 5*e* provide for a positive connection with the corresponding or negatively embodied first coupling element 6, respectively, of the closure part 4 (see FIGS. 1*b* and 1*c*). The cross section shown in FIG. 5*f* requires a frictional connection or a clamping, respectively, of the second coupling element 8, which is formed in a pin-like manner, by means of the first coupling element 6 of the closure part 4, which is embodied negatively or so as to correspond, respectively. Reference numeral 10 identifies a preferably circumferential collar, which particularly preferably serves as sealing means or has a sealing means, respectively, and/or acts as stop.

FIGS. 2*a* to 2*d* show an exemplary embodiment, according to which the first coupling element 6, which is arranged or embodied on the closure part 4, respectively, is embodied in a pin-like manner. The second coupling element 6, which is formed or arranged on the element for the manual contacting 3 and force application or introduction, respectively, is hereby formed negatively or so as to correspond to the first coupling element 6, respectively.

FIGS. 3*a*-3*d* schematically show an embodiment, according to which the first coupling element 6 and the second coupling element 8 are embodied so as to be flat or substantially flat, respectively. It is possible hereby that the first coupling element 6 and the second coupling element 8 are in each case formed by a magnet. In the alternative or in addition, it is possible that the first coupling element 6 and the second coupling element 8 form a hook-and-loop fastener.

Figure 1C:
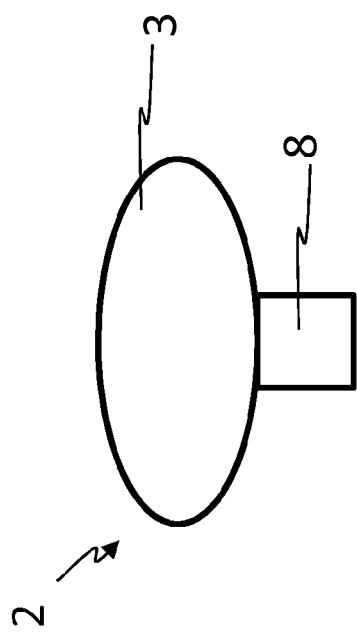
FIG. 1c shows a schematic side view of a first exemplary multi-part safety closure for a hot-water bottle according to the invention.
Figure 1D:
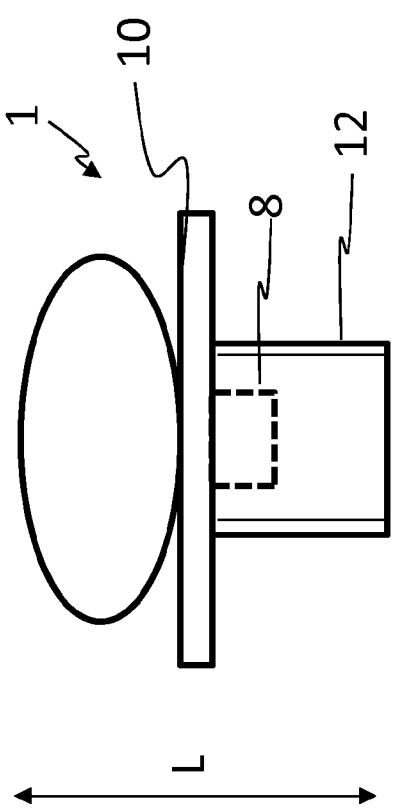
FIG. 1d shows a schematic top view onto a first exemplary multi-part safety closure for a hot-water bottle according to the invention.
Figure 4:
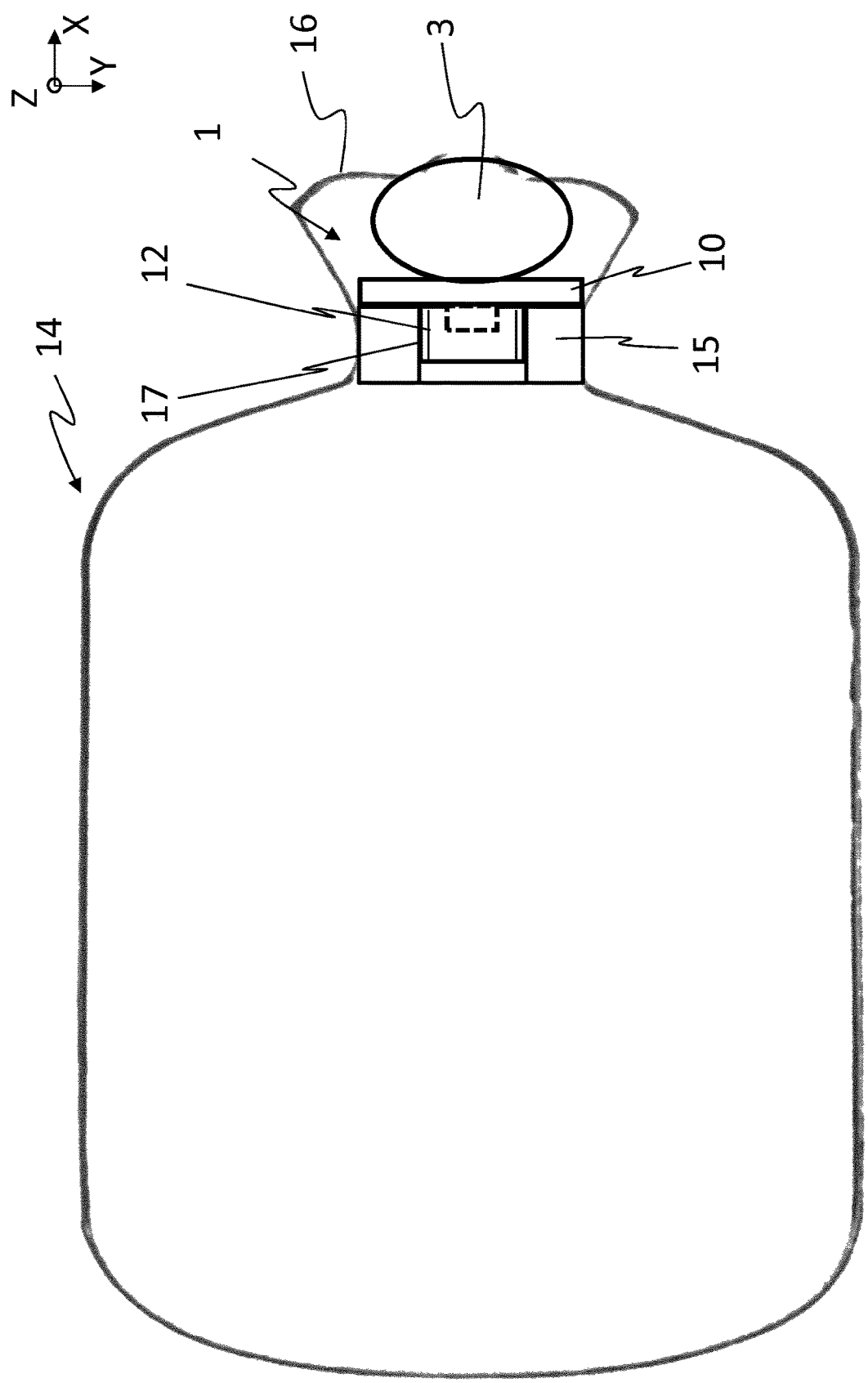
FIG. 4 shows a hot-water bottle with the multi-part safety closure for a hot-water bottle according to the invention shown merely in an exemplary manner in FIG. 1c.

FIG. 4 shows a hot-water bottle 14 according to the invention with an example of a multi-part safety closure for a hot-water bottle 1 according to the invention, in particular the multi-part safety closure for a hot-water bottle shown in FIG. 1*c*.

FIG. 5*i* shows a manual actuating element 2, which is embodied so as to correspond to the closure part 4 from FIG. 5*j*. Likewise, FIG. 5*g* shows a manual actuating element 2, which is embodied so as to correspond to the closure part 4 shown in FIG. 5*h*. In both cases, the first force transmission element 6 and the second force transmission element 8 each have a plurality, in particular at least 2, at least 3, at least 4, at least 5, at least 6, at least 7, at least 10 or at least 15 of partial force transmission elements 100, 101, which are at least partially and preferably completely spaced apart from one another, wherein the partial force transmission elements 100 of the first force transmission element 6 are embodied so as to correspond, in particular negatively, to the partial force transmission elements 101 of the second force transmission element 8. The partial force transmission elements 100 are preferably created as part of the closure part 4 and the partial force transmission elements 101 are preferably created as part of the manual actuating element 2, in particular in an injection molding process.

Figure 6:
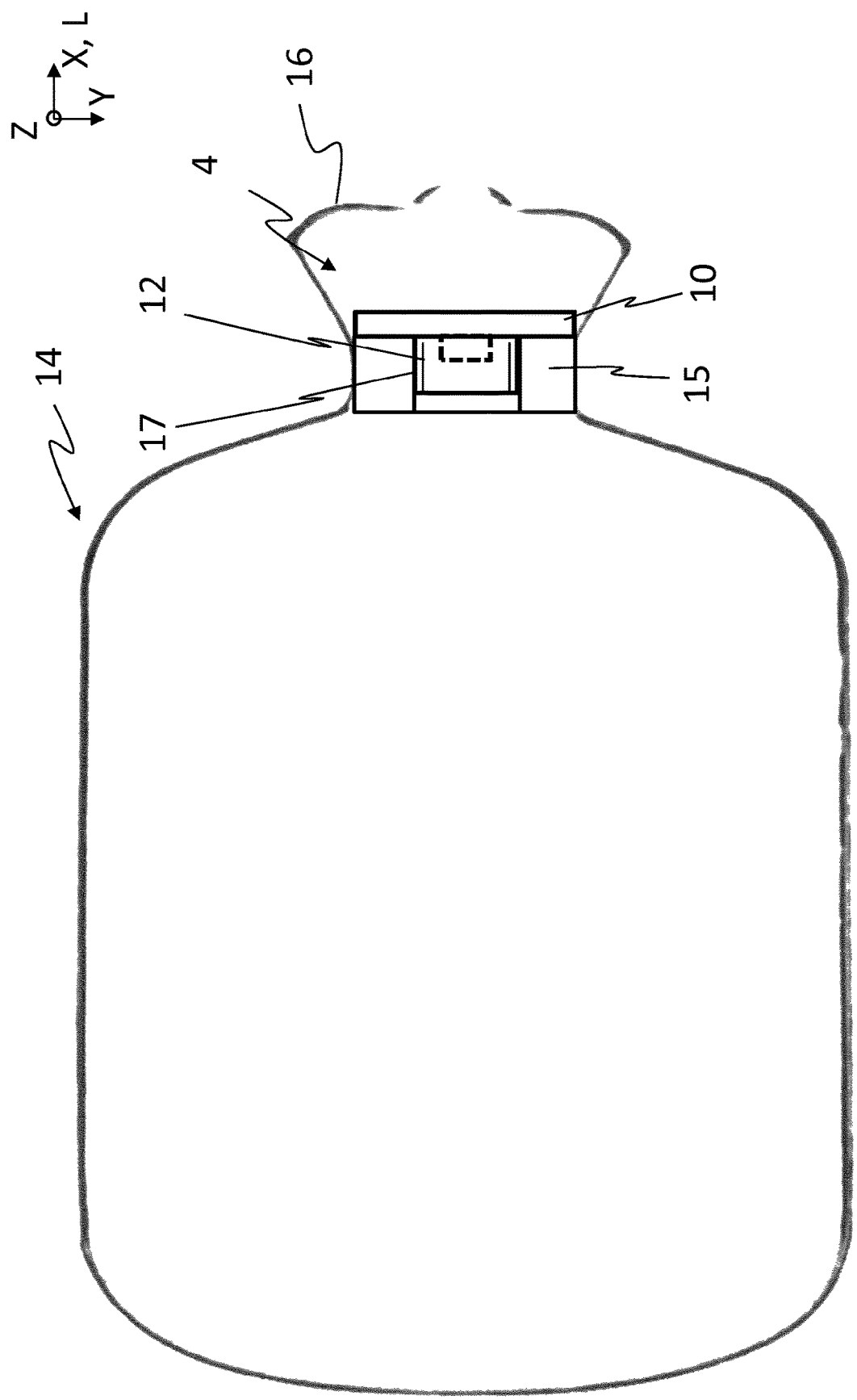
FIG. 6 shows a hot-water bottle closed according to the invention, which cannot be used by third parties in an unauthorized manner.

FIG. 6 shows a hot-water bottle 14, which is closed according to the invention, which cannot be opened by third parties in an un-authorized manner, as long as the manual actuating element 2, which is not illustrated here, is not made accessible to the third party or parties. The closure part 4 is hereby designed in such a way that it is not possible for a person (only using the hands) to open the hot-water bottle, because the forces required for rotating or opening the closure part 4, respectively, cannot be introduced into the closure part 4 or cannot be applied by a person, respectively.

FIG. 7a shows a perspective view of a closure part 4 according to the invention. It can be seen that the first force transmission element 6 is embodied so as to be curved at least sectionally, in particular mostly or completely.

At least a part of a penetration area of the closure part, into which the second force transmission element 8 can be introduced, is preferably delimited by a wall 92, which at least sectionally and preferably mostly and particularly preferably completely encloses the penetration area 90.

According to a preferred embodiment of the invention at hand, the first force transmission element 8 is formed by a wall, in particular an enclosing wall 92, wherein the wall 92 delimits a penetration area 92, in particular a recess 5, wherein the penetration area 92, in particular the recess 5, preferably describes a strip-shaped, in particular a circumferential contour, wherein the recess 5 preferably extends less than 10 mm, in particular less than 9 mm or less than 8 mm or less than 7 mm or less than 6 mm or less than 5 mm or less than 4 mm or less than 3 mm, in particular between 0.5 mm and 2.9 mm, such as, e.g. between 1 mm and 2 mm, orthogonally to the contour. The first force transmission element 8 is preferably embodied in such a way that it can cooperate with the second force transmission element 6 of the closure part 4 via an outer force transmission surface 61 and/or via an inner force transmission surface 62.

The recess 5 is preferably designed to be so narrow or large and is preferably curved in such a way that devices, such as knives or coins, which are not intended for actuating the closure part 4, cannot be used to open the closure.

FIG. 7b shows a perspective view of a manual actuating element 4 according to the invention. It can be seen that the second force transmission element 8 is embodied so as to be curved at least sectionally, in particular mostly or completely.

At least sections of the second force transmission element 8 have an external wall 79, which can be coupled to the enclosing wall 92 of the penetration area 90.

According to a preferred embodiment of the invention at hand, the second force transmission element 8 is formed by a wall, wherein the wall has a thickness of less than 10 mm, in particular of less than 9 mm or of less than 8 mm or of less than 7 mm or of less than 6 mm or of less than 5 mm or of less than 4 mm or of less than 3 mm, in particular between 0.5 mm and 2.9 mm, such as, e.g. between 1 mm and 2 mm. The second force transmission element 8 is preferably designed in such a way that it can cooperate with the first force transmission element 6 of the closure part 4 via an outer force transmission surface 81 of the exterior wall and/or via an inner force transmission surface 82 of an interior wall 80.

At least the outer force transmission surface 81 of the second force transmission element 8 preferably cooperates with the outer force transmission surface 61 of the first force transmission element 6 and/or at least the inner force transmission surface 82 of the second force transmission element 8 cooperates with the inner force transmission surface 62 of the first force transmission element 6. Wherein it goes without saying that it is possible for the closure part 4 to only have an outer force transmission surface 62, 61. According to the manual actuating element 2.

Wherein an outer force transmission surface of the wall 92, which delimits the penetration area 90 in an enclosing manner, is preferably spaced apart further away from an axis of rotation of the closure part or manual actuating element than an outer force transmission surface of the elevation, wherein the respective component is rotated about the axis of rotation in response to the opening and closing of a hot-water bottle. Outer force transmission surfaces 61, 62 are located on the side (exterior) of the closure part 2, which can be accessed when the closure part 2 is screwed into the hot-water bottle, and inner force transmission surfaces 160, 161 are located on the side (interior) of the closure part 2, which cannot be accessed when the closure part 2 is screwed into the hot-water bottle is screwed in, i.e. inside the threaded piece 15.

FIGS. 8a-8c show three different illustrations of examples for the closure parts 4 according to the invention. The penetration area 90 of the individual closure parts 4, however, is different. FIGS. 8a and 8b show closure parts having an elevation 94, whereas FIG. 8c does not have such an elevation, thus also not an outer circumferential wall 60 of the elevation 94. According to FIGS. 8a and 8b, the penetration area can be embodied so as be partially, sectionally, completely or mostly tapered. It is also possible, however, that the penetration area is delimited by walls 92, 60, which are preferably oriented parallel to one another or which are oriented at an incline. Reference numeral 96 identifies a tapering portion of the penetration area 90.

The exemplary manual actuating elements 2, which are illustrated in an exemplary manner by means of FIGS. 8d-8f, in each case have a handle part 3. The examples illustrated by FIGS. 8e and 8f further have interior walls 80 for forming force transmission surfaces 82. It is thus possible for the second force transmission means 8 (of the manual actuating element 2) to only introduce forces or momentum, respectively, for screwing in or unscrewing the closure part 4 into the first force transmission element 6 (of the closure part 4) via the interior wall 80. In the alternative, however, it is possible that the forces are transmitted via the interior surface 80, 82 and the exterior wall 79. It is further possible that the forces and momentum are only transmitted via the exterior surface. FIG. 8d shows, e.g., a manual actuating element 2, which does not have an interior surface for transmitting forces and momentum and which thus transmits forces and momentum only via the exterior surface 79.

It is furthermore possible that each of the shown manual actuating elements 2 is able to cooperate with a closure part according to FIG. 8c. It is further possible for manual actuating elements according to FIGS. 8e and 8f to be able to cooperate with closure parts 4 according to FIGS. 8a and 8b.

The closure part 4 and the manual actuating element 2 are thus preferably held in a coupled state, in particular frictionally or by a positive connection or magnetic connection by means of the cooperation of the first force transmission element 6 and of the second force transmission element 8. A point pressure or a line pressure or surface pressure can preferably be created between the first force transmission element 6 and the second force transmission element 8, by means of which the frictional connection is preferably created. This is advantageous, because the closure part 4 is tension-loaded by means of the manual actuating element 2 when unscrewing the closure part 4, and is thus held directly by the manual actuating element 2 at the moment of complete unscrewing. This is extremely helpful, because the user thus holds an object in his hand and can stow it more easily. At the moment of unscrewing, the closure part 4 further does not drop down, whereby there would be the risk of loss.

According to a further preferred embodiment of the invention at hand, the distance A between the elevation surface 62 of the wall 60 of the elevation 94 (or elevation wall 60) and the outer force transmission surface 61 of the enclosing wall 92 is less than 12 mm, in particular less than 11 mm or less than 9 or less than 8 mm or less than 7 or less than 6 mm or less than 5 mm or less than 4 mm or less than 3 mm or less than 2 mm, in particular less than 1.5 mm or 1 mm. The elevation 94 and the enclosing wall 92 preferably have the same height or substantially the same height.

The second force transmission element 8 can preferably be coupled to the first coupling element 6 via the wall 60 of the elevation 94 and/or via the outer force transmission surface 61 of the enclosing wall 92.

A surface of the wall 92, which is directed in the direction of the center of rotation of the closure part, is hereby preferably identified as outer force transmission surface 61, and a surface of the wall 60 of the elevation 94, which is directed to the outside (in particular radially outside) and at least sections of which are surrounded by the outer force transmission surface 61, is hereby preferably identified as outer force transmission surface 62.

The elevation 94 is preferably designed in such a way that the introduction of a torque of 2 Nm+/−0.1 Nm into the closure part 2 for the water-tight sealing and for opening a hot-water bottle requires an application of force to the elevation 94 with a force of more than 50 N, in particular of more than 60 N or of more than 70 N, wherein the elevation 94 according to a preferred embodiment, in particular according to this embodiment, does not protrude or protrudes only slightly in the longitudinal direction L of the closure part 2 beyond the collar surface 13, which delimits the collar 10 in the longitudinal direction L, in the longitudinal direction L, in particular up to 7 mm or up to 6 mm or up to 5 mm or up to 4 mm or up to 3 mm or up to 2 mm or up to 1 mm. In addition or in the alternative, at least sections of the second force transmission element have an exterior wall 79, which can be coupled to the enclosing wall 92 of the penetration area 90, wherein, in addition to the enclosing wall 92, the penetration area 90 is preferably also delimited by means of at least one wall 60 by at least one elevation 94, in particular a pin-like or column-like element, which is formed by at least one area, which is delimited by the enclosing wall 92.

FIG. 9a shows a top view onto an example of a closure part 2 according to the invention. The closure part 4 has a penetration area 90 for receiving the manual actuating element 2. According to this special embodiment, the penetration area 90 is delimited on the one hand by means of a wall 92, which encloses the penetration area. On the other hand, the penetration area 90 is delimited by a wall 60, which is formed by an elevation 94. In the alternative, however, it is hereby also possible for the wall 60 and thus the elevation 90 not to be formed. Reference numeral 10 identifies the collar of the closure part 4.

FIG. 9b shows a perspective bottom view of the closure part known from FIG. 9a. It can be gathered from the illustration that a plurality of, in particular more than two hollow spaces 30-35, preferably more than 3, and particularly preferably more than 4, such as, e.g. 5 or 6, are embodied between the wall 92 and a circumferential wall 28, which has the thread. On the closure part underside, at least sections of the wall 92, which encloses the penetration area 90, are thus spaced apart from a circumferential wall 28, which has the thread, whereby the plurality of free spaces 30-34, which are delimited from one another, are embodied between the circumferential wall 28, which has the thread, are and the wall 92, which encloses the penetration area 90, or a circumferential free space is embodied between the enclosing wall 92 and the circumferential wall 28, which has the thread. The free spaces 30-34 or the free space 35 preferably result from a maximum wall thickness of the enclosing circumferential wall 28, wherein the maximum wall thickness is less than 5 mm, is in particular less than 4 mm or is less than 3 mm or is less than 2 mm. In addition or in the alternative, the collar 10 is formed by a collar wall, which has at least a thickness of 1 mm or of 1.5 mm or of 2 mm and preferably of at least 2.5 mm or of at least 2.8 mm or of at least 3.0 mm or of at least 3.3 mm or of at least 3.45 mm or of at least 3.55 mm or of at least 3.6 mm or of at least 3.65 mm or of at least 3.7 mm or of at least 3.75 mm in the longitudinal direction L.

FIG. 9b and FIG. 9c further illustrates a seal 13 or a sealing element 13, respectively. The seal or the sealing element, respectively, is preferably part of the collar 10, is in particular formed in one piece therewith. For sealing the hot-water bottle, the seal 13 or the sealing element 13, respectively, preferably cooperates with a threaded piece 15 by pressing or, for sealing purposes, cooperates with a portion of the material, which forms the hot-water bottle body by pressing. At least sections of the threaded piece 15 are preferably surrounded by the material, which forms the hot-water bottle body, at least sections of the threaded piece 15 are preferably in particular insert molded by the material. For sealing purposes, the seal 13 or the sealing element 13, respectively, particularly preferably cooperates with the material of the hot-water bottle body, which surrounds the threaded piece.

FIG. 10a shows a cross section through the closure part 4 shown in FIG. 9a. It can be seen that the penetration area 90 in this embodiment is delimited by the wall 92, which encloses the penetration area on the outside. In this embodiment and preferably in all other embodiments, which have a penetration area 90, this wall is at least 0.8 mm thick and preferably at least 1 mm thick and particularly preferably at least 1.2 mm thick or at least 1.5 mm thick or at least 1.8 mm thick or at least 2 mm thick. The wall is preferably maximally 5 mm thick and particularly preferably maximally 3 mm thick or maximally 2.5 mm thick or maximally 2 mm thick or maximally 1.5 mm thick. In the cross sectional illustration, the outer surface 61 of the wall 92 is preferably embodied so as to be inclined with respect to the surface 11, is in particular formed at an angle of between 60° and 90° and is preferably formed at an angle of between 70° and 89° or between 80° and 88°.

The wall 60, which forms the elevation 94, is preferably at least 0.8 mm thick and preferably at least 1 mm thick and particularly preferably at least 1.2 mm thick or at least 1.5 mm thick or at least 1.8 mm thick or at least 2 mm thick. The wall 60 is preferably maximally 5 mm thick and particularly preferably maximally 3 mm thick or maximally 2.5 mm thick or maximally 2 mm thick or maximally 1.5 mm thick. In the cross sectional illustration, the outer surface 62 of the wall 60 is preferably embodied so as to be inclined with respect to the surface 11, in particular formed at an angle of between 60° and 90° and is preferably formed at an angle of between 70° and 89° or between 80° and 88°.

The wall 92 is preferably directly connected to the wall 60 or via a connecting wall 64 or a connecting wall portion 64, respectively. The connecting wall 64 is preferably at least 0.8 mm thick and preferably at least 1 mm thick and particularly preferably at least 1.2 mm thick or at least 1.5 mm thick or at least 1.8 mm thick or at least 2 mm thick. The connecting wall 64 is preferably maximally 5 mm thick and particularly preferably maximally 3 mm thick or maximally 2.5 mm thick or maximally 2 mm thick or maximally 1.5 mm thick.

The wall 92 further has an inner surface 161. In the cross sectional illustration, the inner surface 161 of the wall 92 is preferably embodied so as to be inclined with respect to the surface 11, it is in particular formed at an angle of between 60° and 90° and is preferably formed at an angle of between 70° and 89° or between 80° and 88°.

The wall 60 further has an inner or interior surface 160, respectively. In the cross sectional illustration, the inner surface 160 of the wall 60 is preferably embodied so as to be inclined with respect to the surface 11, is in particular formed at an angle of between 60° and 90° and is preferably embodied at an angle of between 70° and 89° or between 80° and 88°.

Reference numeral 151 identifies the interior wall of the threaded section.

FIG. 10b specifies preferred examples for dimensions. The height H hereby preferably identifies the thickness of the wall portion identified with 941. The wall portion 941 preferably as a height H1 of preferably at least 0.8 mm and preferably of at least 1 mm and particularly preferably of at least 1.2 mm or at least 1.5 mm or at least 1.8 mm or at least 2 mm. The wall portion 941 preferably maximally has a height H1 of 5 mm and particularly preferably of maximally 3 mm or of maximally 2.5 mm or of maximally 2 mm or of maximally 1.5 mm.

The height H2 hereby preferably identifies the height of the penetration area 90. The penetration area 90 preferably has a height H2 of preferably at least 0.8 mm and preferably at least 1 mm and particularly preferably at least 1.2 mm or at least 1.5 mm or at least 1.8 mm or at least 2 mm or at least 3 mm or at least 4 mm or at least 5 mm. The penetration area 90 preferably maximally has a height H2 of 15 mm and particularly preferably of maximally 12 mm or of maximally 10 mm or of maximally 8 mm or of maximally 5 mm or of maximally 2 mm.

FIG. 11a show a schematic perspective illustration of a closure part attachment element 302 or of a closure part attachment element 302 of a safety closure for a hot-water bottle, respectively. The closure part attachment element 302 hereby has at least one functional means 306, wherein the functional means 306 forms a functional area 308 (see FIG. 11b, 11m or 12b), wherein the functional area 308 is formed by at least sectional overlapping of a force transmission element 6 of a closure part 4 for a safety closure for a hot-water bottle. Preferably, one or exactly one or at least one positioning means 304 is arranged or formed, respectively, on the or in the (in particular as magnetic portion) or as part of the functional means 306. However, it is hereby also possible for a plurality of positioning means 304 to be arranged of formed, respectively, on the functional means 306. The positioning element 304 is preferably arranged of formed, respectively, on a first side 310 or on a first side of the functional means 306, or the positioning elements are arranged or formed, respectively, on a first side 310 or on a first side of the functional means 306. On the side located opposite the first side 310, the functional means 306 is preferably delimited by the second side 312. The second side 312 thereby forms a surface, which is flat, preferably in sections or completely. In the alternative, however, it is also possible that the surface formed by the second side 312 embodies an at least sectionally three-dimensional structure (see, e.g., FIG. 11d or 12a). The second side 312 thereby preferably forms a coupling surface 314 (FIG. 11a) or coupling structure 314 (FIG. 12a).

It is further possible hereby that the functional means 306 is formed magnetically or has at least or exactly one magnetic element or a magnetic portion. An element, which is also magnetically active, can then preferably be magnetically coupled to the closure part attachment element 302 via the second side 312. In addition or in the alternative, it is possible for the second side 312 to be formed in such a way that a further element can be releasably or non-releasably arranged thereon by material connection or in a positive or frictional manner.

FIG. 11b shows a side view of the illustration of FIG. 11a.

FIG. 11c shows a side view of an assembly of a closure part 4 or a closure part 4 for a safety closure for a hot-water bottle, respectively, according to the invention, with a further example of a closure part attachment element 302 according to the invention. It can be gathered from this illustration that, in a state, in which the closure part attachment element 302 is coupled to the closure part 4 for the safety closure for a hot-water bottle, the functional means 306 is preferably visible or touchable or accessible, preferably on a second side 312 (see FIG. 11b), which differs from the first side 310 and which is preferably located substantially or exactly parallel to the first side 310. In the state, in which the closure part attachment element 302 is coupled to the closure part 4 of a safety closure for a hot-water bottle, the first side 310 of the functional means 306 is preferably at least partially invisible or untouchable or inaccessible or covered.

FIG. 11d shows a sectional illustration of the assembly shown in FIG. 11c. The section thereby runs according to the cutting line identified in FIG. 11c by "A". It can be gathered from this illustration that the functional means 306 can have electronic means 316. It is hereby in the spirit of the invention at hand, that preferably one, exactly one or at least one electronic means 316 is provided, whereby it is also possible that two, exactly two or more than two electronic means 316 are provided, in particular to be completely or partially embedded in the functional area 308. It is thus possible that an electronic means 316 protrudes beyond the first side or surface 310, respectively, and/or beyond the second side or the surface 312, respectively, of the functional means 306 or to adjoin it. It is furthermore possible that an electronic means 316 or a plurality of electronic means 316 is/are exclusively or completely formed, respectively, between the first side 310 and the second side 312. The electronic means 316 is preferably a sensor means, in particular having a temperature sensor and/or brightness sensor or light sensor, respectively and/or humidity sensor and/or motion sensor, and/or an accumulator and/or a processor device and/or a communication device, in particular Bluetooth, and/or a display and/or an acoustic output device and/or a source of radiation, in particular a light source, in particular an LED light, and/or a device for producing electrical energy, in particular a solar cell device and/or a piezo element device, in particular having one or a plurality of piezo elements. Preferably, the electronic means 316 is a device, which has a plurality of the above-mentioned components and/or devices.

FIG. 11e shows a closure part attachment element 302, which is preferably embodied as thermally insulating closure cover. The closure part attachment element 302 can hereby be coupled, preferably frictionally, to the collar 10 of a closure part 4 according to the invention, by means of a fixing area 308, which is preferably embodied as at least sectionally and particularly preferably completely circumferential positioning element 304.

FIG. 11g shows a state, in which the closure part attachment element 302 shown in FIGS. 11e and 11f is arranged on a closure part 4 according to the invention.

FIG. 11h shows an example of further closure part attachment elements 302, which can in each case cooperate with or can be coupled to, respectively, a correspondingly embodied force transmission element 6 of a closure part 4. Such dependent designs are advantageous, because momentum can be introduced into the force transmission element 6 or the force transmission elements 6, respectively, of the closure part 4 by means of the cooperation of the positioning element 304 or of the positioning elements 304. The coupling alternative via the collar 10 of the closure part 4, which is at least schematically illustrated in FIGS. 11e to 11g, is further advantageous, because it is independent from the respective design of the force transmission element 6 of the closure part 4.

FIG. 11i shows a sectional illustration of a further preferred example of a closure part 4 for a safety closure for a hot-water bottle. According to this example, the closure part 4 has a central coupling location 318, which, in its center, extends from the side of the surface 11 delimiting the collar 10 on the upper side, into the area, which is surrounded by the thread 12. The coupling location 318 is thereby preferably part of the wall 319, which seals the closure part 4 upwards, in particular in axial direction. The surface 321 of the coupling location 318 preferably forms an at least sectionally conical or pin-shaped design.

FIG. 11k shows a top view onto the closure part 4 shown in FIG. 11i.

FIG. 11l shows a schematic bottom view of a further example of a closure part attachment element 302 according to the invention. Reference numeral 308 hereby identifies the first side of the functional means 306 or an underside of the functional means 306, respectively, of the closure part attachment element 302. It can furthermore be seen that a positioning means 304, which is preferably embodied so as to correspond to a coupling location 318 of a closure part 4, is preferably embodied or arranged, respectively, centrally on the underside 310 of the functional means 306.

FIG. 11m shows a schematic side view of the closure part attachment element 302 shown in FIG. 11l.

It furthermore applies for all closure part attachment elements 302 that the shape of the functional means 306 can differ from a round, in particular disk-like shape.

FIG. 12a shows a schematic illustration of a top view onto a second side 32, in particular an outer surface of a functional means 306 of a further preferred closure part attachment element 302. The second side 312 of the functional means 306 hereby preferably forms a coupling surface 314, which is designed three-dimensionally. The coupling surface 314 preferably serves for coupling to a further element, in particular for coupling to a manual actuating element or a manual actuating element 2 for a safety closure for a hot-water bottle, respectively. The coupling surface 314 thereby preferably forms a cross-like shape. It is hereby possible, however, that the coupling surface 314 forms a shape, which differs from a cross-like shape.

FIG. 12b shows a side view of the closure part attachment element 302. In combination with FIG. 12a, it can be seen that the cross-shaped coupling surface 314, which is visible in FIG. 12a, is embodied as depression in the functional means 306 or functional area 308, respectively. In the alternative, however, it is also possible that the coupling surface 314 or a three-dimensional coupling structure 314, respectively, can be embodied so as to protrude. Preferably at least one positioning means 304 adjoins the functional area 308 or the functional means 306, respectively. The positioning means 304 is preferably embodied negatively to a force transmission element 6 of the closure part 4. According to this illustration, the positioning means 304 is embodied in a star-shaped manner, wherein, in the alternative, it can also have different shapes, in particular different shapes, which differ from a circle or ring.

FIG. 12c shows a top view onto the underside 310 of the closure part attachment element 302 shown in FIGS. 12a and 12b.

FIG. 12d shows the closure part attachment element 302, which is already illustrated in FIGS. 12a-c, in a perspective view.

Merely in an exemplary manner, FIG. 12e shows the illustration of a closure part 4, which is also shown in FIG. 10a.

FIG. 12f shows a sectional illustration of an assembly of the closure part attachment element 302 shown in FIG. 12d, and of the closure part 4 shown in FIG. 12e.

The or a closure part attachment element 302, respectively which is designed according or analogously to FIGS. 12a-12d, respectively, can preferably also be identified as intermediate member or adapter.

Particularly preferably, at least parts of the closure part attachment element 302 are injection molded parts or 3D printing components. The closure part attachment element 302 preferably consists at least partially of a polymer material, in particular PE, PA, PLA or a combination thereof.

FIGS. 13a-d show different, at least germ-reduced, in particular sterile, packaged objects according to the invention. It is also possible hereby that all possible combinations of the objects shown in these figures can be arranged in a packaging in a germ-reduced, in particular sterile manner. Preferably, the packaging 200 shown in these figures is packaging, which, in terms of volume or in terms of mass, at least partially or mostly or completely consist of a polymer material, in particular of polypropylene or polyamide or polyethylene or of a combination of at least two of these materials or have them, respectively.

Reference numeral 202 identifies a germ-reduced, in particular sterile area, which is delimited by the packaging 200.

Figure 13A:
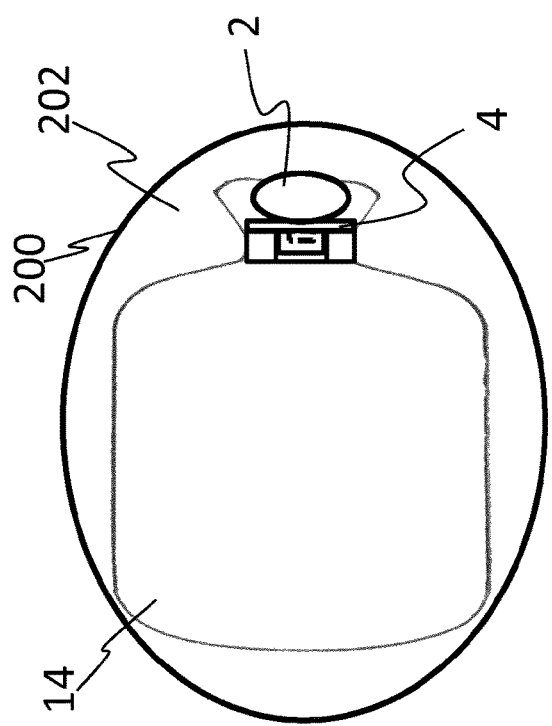
Figure 13B:
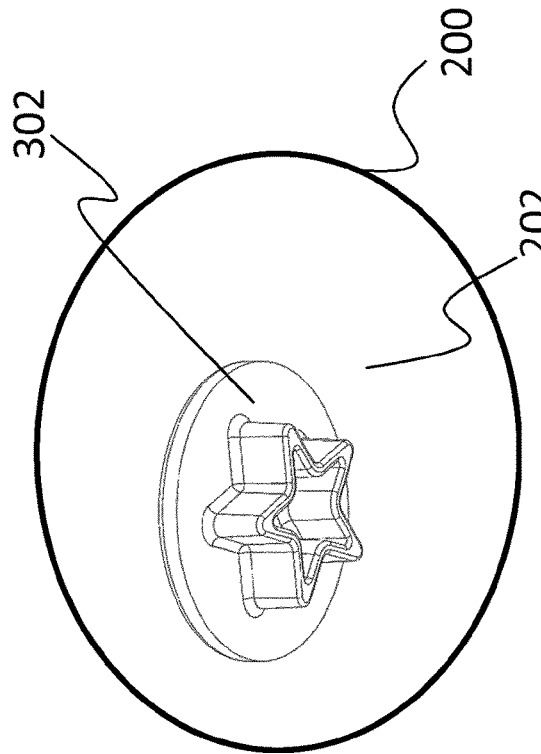
Figure 13C:
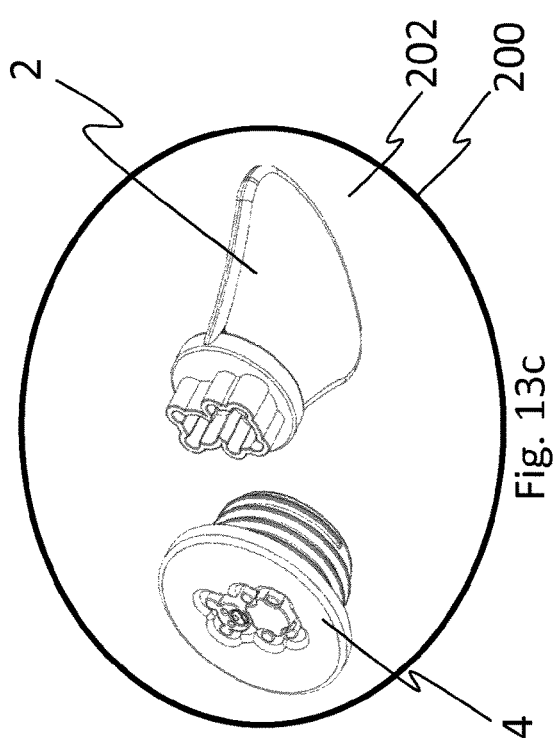
Figure 13D:
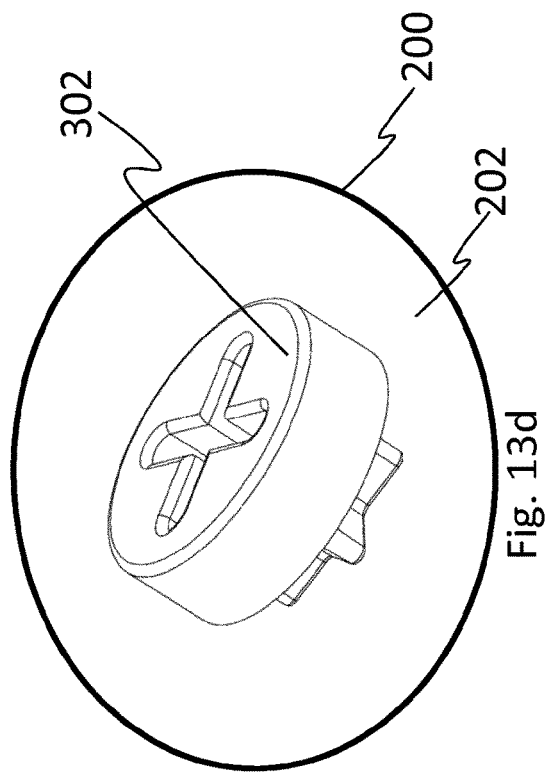

In FIG. 13a, the shown objects are a hot-water bottle 14 having a multi-part safety closure for a hot-water bottle 1, in FIG. 13b a closure part attachment element 302, in FIG. 13c a closure part 4 for a safety closure for a hot-water bottle and a manual actuating element 2 for a safety closure for a hot-water bottle, and in FIG. 13d a further closure part attachment element 302, in particular an adapter. Provision can further preferably also be made in one of this packaging 200 for a hot-water bottle cover, in particular having a textile material.

The packaging 200 can preferably be opening after the introduction of an object and subsequent sealing, particularly preferably only as a result of a destruction of the packaging, i.e. an elimination of the germ reduction or an elimination of a sterile state, respectively, for removing the respective object.

LIST OF REFERENCE NUMERALS 1 multi-part safety closure for a hot-water bottle
2 manual actuating element or manual actuating element for a safety closure for a hot-water bottle
3 element for manual contacting
4 closure part or closure part for a safety closure hot-water bottle
5 recess
6 first force transmission element
8 second force transmission element
10 collar
11 surface delimiting collar in longitudinal direction 1
12 external screw thread
13 circumferential sealing element -continued

| | |
|---|---|
| 14 | hot-water bottle |
| 15 | threaded piece |
| 16 | funnel |
| 17 | internal screw thread of the threaded piece |
| 28 | circumferential wall having external screw thread |
| 30 | first hollow space or first depression, respectively |
| 31 | second hollow space or second depression, respectively |
| 32 | third hollow space or third depression, respectively |
| 33 | fourth hollow space or fourth depression, respectively |
| 34 | fifth hollow space or fifth depression, respectively |
| 35 | central hollow space or central depression, respectively |
| 60 | wall of the elevation |
| 61 | external force transmission surface of the first force transmission element or of the enclosing wall 92, respectively |
| 62 | external force transmission surface of the wall of the elevation |
| 64 | connecting wall |
| 79 | external wall portion of thesecond force transmission element |
| 80 | internal wall portion of the second force transmission element |
| 81 | external force transmission surface of the second force transmission element |
| 82 | internal force transmission surface of the second force transmission element |
| 90 | penetration area of the first force transmission element |
| 92 | enclosing wall of the first force transmission element or enclosing wall of the first force transmission element |
| 94 | elevation of the first force transmission element |
| 96 | tapering portion |
| 98 | increasing portion |
| 100 | partial force transmission element of the closure part |
| 101 | partial force transmission elements of the manual actuating element |
| 151 | interior wall of the threaded section |
| 160 | interior surface of the wall portion 60 |
| 161 | interior surface of the wall portion 92 |
| 200 | packaging |
| 202 | receiving area |
| 300 | closure part underside |
| 302 | closure part attachment element or closure part attachment element of the safety closure for a hot-water bottle |
| 304 | positioning element |
| 306 | functional means |
| 308 | functional area |
| 310 | first side of the functional means |
| 312 | second side of the functional means |
| 314 | coupling surface |
| 316 | electronic means |
| 318 | central coupling location |
| 941 | central wall portion of the elevation |
| A | distance |
| L | longitudinal direction |
| H1 | height 1 |
| H2 | height 2 |

The invention claimed is:

1. A multi-part safety closure for a hot-water bottle, comprising:
a closure part having an external screw thread defined on a circumferential wall that extends in a longitudinal direction L and configured to screw into an internal screw thread of the hot-water bottle, and having a first force transmission element for transmitting momentum for screwing the closure part into the internal screw thread of the hot-water bottle to seal the hot-water bottle in a water-tight manner and for unscrewing the closure part from the internal screw thread of the hot-water bottle; and
a manual actuating element having a second force transmission element for transmitting to the closure part the momentum required to screw the closure part into the internal screw thread of the hot-water bottle and to unscrew the closure part from the internal screw thread of the hot-water bottle,
wherein:
the first force transmission element and the second force transmission element are configured such that the closure part is operably connectable with the manual actuating element in a detachable manner,
the first force transmission element is embodied as an internal force transmission element and is embodied by surrounding wall portions,
the second force transmission element is embodied to at least partially penetrate into the internal force transmission element,
at least a part of a penetration area of the closure part, into which the second force transmission element is insertable, is delimited by an enclosing wall that at least partially encloses the penetration area,
on a first side of the closure part that is configured to face an interior of the hot-water bottle, at least sections of the enclosing wall, which encloses the penetration area, are spaced apart from the circumferential wall such that a plurality of free spaces, which are delimited from one another, are defined between the enclosing wall and the circumferential wall or a circumferential free space is defined between the enclosing wall and the circumferential wall,
the closure part further includes:
a circumferential collar attached to the circumferential wall and configured as a stop that delimits a maximum screw-in depth of the closure part into the internal screw thread of the hot-water bottle,
a circumferential sealing element formed as a first elevation having a curved contact surface that is a one-piece part of the collar and thus of the closure part, and
wherein:
a surface of a second side of the closure part in the longitudinal direction L also delimits a surface of the circumferential collar in the longitudinal direction L,
a second elevation is embodied on the closure part and is at least partially enclosed by the enclosing wall, and
a distance (A) between a wall of the second elevation and the enclosing wall is less than 12 mm, the second elevation and the enclosing wall having the same height or substantially the same height, or
the second elevation is configured such that the application of a torque of 2 Nm+/−0.1 Nm to the closure part for the water-tight sealing and for opening the hot-water bottle requires application of a force of more than 50 N to the second elevation, wherein the second elevation does not protrude or protrudes only slightly in the longitudinal direction (L) of the closure part beyond the collar surface, or
at least sections of the second force transmission element have an exterior wall and are configured to be coupled to the enclosing wall of the penetration area, wherein, in addition to the enclosing wall, the penetration area is also delimited by the wall of the second elevation, which is formed in the area delimited by the enclosing wall.

2. A hot-water bottle comprising:
a flexible material defining a container for holding hot water connected to a funnel via a neck portion, and
the multi-part safety closure according to claim 1, wherein the external screw thread is screwed into an internal screw thread defined in the neck portion.

3. The hot-water bottle according to claim 2, wherein the closure part is configured to seal the neck portion in a water-tight manner in a state in which the manual actuating element is removed from the closure part.

4. The hot-water bottle according to claim 3, wherein:
the second force transmission element has a shape of a hollow star; and
the penetration area is configured as a star-shaped trough in the second side of the closure part that is complementary to the shape of the hollow star of the second force transmission element.

5. The hot-water bottle according to claim 4, wherein:
the circumferential collar has a wider diameter than the external screw thread,
the plurality of free spaces are formed on the first side of the closure part between the circumferential wall and enclosing walls that define radially outer wall surfaces of the star-shaped trough,
another free space is defined within radially inner wall surfaces of the star-shaped trough, and
each of the free spaces is a hollow space.

6. The hot-water bottle according to claim 5, wherein a width of the star-shaped trough is narrower than a width of the hollow star such that a press fit or clamp fit is formed when the hollow star is inserted into the star-shaped trough.

\* \* \* \* \*